(12) United States Patent
Hong et al.

(10) Patent No.: US 11,633,413 B2
(45) Date of Patent: *Apr. 25, 2023

(54) COMPOSITION FOR PREVENTING OR IMPROVING MENOPAUSAL SYMPTOM COMPRISING NOVEL GINSENOSIDE

(71) Applicant: AMOREPACIFIC CORPORATION, Seoul (KR)

(72) Inventors: Yong Deog Hong, Yongin-si (KR); Hyun Woo Jeong, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/031,057

(22) Filed: Sep. 24, 2020

(65) Prior Publication Data

US 2021/0093653 A1    Apr. 1, 2021

(30) Foreign Application Priority Data

Sep. 27, 2019    (KR) .......................... 10-2019-0119642

(51) Int. Cl.
    *A61K 31/7048*    (2006.01)
    *A61K 36/258*    (2006.01)
    *A61K 9/00*    (2006.01)

(52) U.S. Cl.
    CPC ........ *A61K 31/7048* (2013.01); *A61K 36/258* (2013.01); *A61K 9/0014* (2013.01); *A61K 9/0019* (2013.01); *A61K 9/0053* (2013.01)

(58) Field of Classification Search
    CPC . A61K 31/7048; A61K 36/258; A61K 9/0014
    USPC ......................................................... 514/53
    See application file for complete search history.

(56) References Cited

FOREIGN PATENT DOCUMENTS

| CN | 1795868 A | 7/2006 |
|---|---|---|
| CN | 1875975 A | 12/2006 |
| CN | 102875628 A | 1/2013 |
| CN | 102924556 A | 2/2013 |
| JP | 2007-512361 A | 5/2007 |
| KR | 10-0178867 B1 | 11/1998 |
| KR | 10-0717872 B1 | 5/2007 |
| KR | 10-1312389 B1 | 9/2013 |
| KR | 10-1568658 B1 | 11/2015 |
| KR | 10-2016-0086149 A | 7/2016 |
| KR | 10-2016-0118481 A | 10/2016 |
| WO | 2005/000245 A2 | 1/2005 |
| WO | 2005/000248 A2 | 1/2005 |
| WO | 2005/040189 A1 | 5/2005 |
| WO | 2005/097141 A2 | 10/2005 |

OTHER PUBLICATIONS

Mainland (Australian Menopause Centre; Nov. 29, 2017).*
Australasian Menopause Society; May 2019.*
Brazier (Medical News Today; Dec. 20, 2015).*
Bailey et al. (J Physiol 594.3 (2016) pp. 657-667).*
Yang Jie, et al., "Semisynthesis and Cytotoxicity Evaluation of a Series of Ocotillol Type Saponins and Aglycones from 20(S)-Ginsenoside Rg2, Rh1, Protopanaxatriol and Their 20(R)-Epimers", Chem. Res. Chin. Univ., 2016, vol. 32, No. 1, pp. 35-40.
CAS RN : 2170771-84-1 (The capture image file of the STN International Database), accessed Jun. 2, 2020.
CAS RN : 2170771-84-1 (The capture image file of the STN International Database), accessed Jul. 2, 2019.
Bonnie J. Deroo, et al., "Estrogen receptors and human disease", J Clin Invest., 2006, vol. 116, No. 3, pp. 561-570.
Heather A. Harris, et al., "Evaluation of an Estrogen Receptor-β Agonist in Animal Models of Human Disease", Endocrinology, 2003, vol. 144, No. 10, pp. 4241-4249.

* cited by examiner

*Primary Examiner* — Shaojia A Jiang
*Assistant Examiner* — Michael C Henry
(74) *Attorney, Agent, or Firm* — Merchant & Gould P.C.

(57) ABSTRACT

The present disclosure relates to a composition comprising (20S,24R)-6-O-β-D-glucopyranosyl(1→2)-β-D-glucopyranoside-dammar-3-one-20,24-epoxy-6a,12b,25-triol, which is a novel ginsenoside, a pharmaceutically acceptable salt thereof, a hydrate thereof or a solvate thereof as an active ingredient. In addition, it relates to a method for preventing or improving menopausal symptoms, which comprises administering an effective amount of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof to a subject in need thereof. The novel ginsenoside has a superior effect of preventing or improving menopausal symptoms with a low risk of breast cancer.

7 Claims, 24 Drawing Sheets

1: $R_1$ = Glc; $R_2$ = H
2: $R_1$ = H; $R_2$ = Rha
3: $R_1$ = Glc; $R_2$ = Rha

4: $R_1$ = Glc; $R_2$ = H
5: $R_1$ = Glc; $R_2$ = Glc
6: $R_1$ = Glc; $R_2$ = Ara

7: R = Glc

8: R = Glc

9: R = Glc

10

11

12

13

14

15

16

Chemical Formula: $C_{42}H_{72}O_{14}$
Exact Mass: 800.4922

1. Ginsenoside Rg1

Chemical Formula: $C_{42}H_{72}O_{13}$
Exact Mass: 784.4973

2. (20S)-Ginsenoside Rg2

Chemical Formula: $C_{48}H_{82}O_{18}$
Exact Mass: 946.5501

3. Ginsenoside Re

Chemical Formula: $C_{48}H_{82}O_{18}$
Exact Mass: 946.5501

4. Ginsenoside Rd

Chemical Formula: $C_{54}H_{92}O_{23}$
Exact Mass: 1108.6029

5. Ginsenoside Rb1

Chemical Formula: $C_{53}H_{90}O_{22}$
Exact Mass: 1078.5924

6. Ginsenoside Rb2

COMPOSITION FOR PREVENTING OR IMPROVING MENOPAUSAL SYMPTOM COMPRISING NOVEL GINSENOSIDE

CROSS-REFERENCE TO RELATED APPLICATION

This application claims priority to Korean Patent Application No. 10-2019-0119642, filed on Sep. 27, 2019, and all the benefits accruing therefrom under 35 U.S.C. sctn.119, the contents of which in its entirety are herein incorporated by reference.

BACKGROUND OF THE INVENTION

Field of the Invention

The present disclosure relates to a novel ginsenoside and a composition comprising the same.

Description of the Related Art

Ginseng (*Panax ginseng* C.A. Meyer) is a plant belonging to the genus *Panax* of the family Araliaceae, which has been used as herbal medicine in Korea, China, Japan, etc. for over 2,000 years. Saponins, polysaccharides, peptides, sitosterols, polyacetylenes and fatty acids are known as representative physiologically active ingredients of ginseng. The saponins of ginseng are called ginsenosides. As the efficacy and effect of ginseng, the action of the central nervous system, anticarcinogenic action and anticancer activity, immunomodulatory action, antidiabetic action, liver function-improving effect, cardiovascular disorder-improving and anti-arteriosclerotic action, blood pressure-regulating action, effect on improvement of menopausal disorder and osteoporosis, anti-stress and anti-fatigue actions, antioxidant activity, antiaging effect, etc. are known. The contents and compositions of ginsenoside vary greatly depending on the part of ginseng, such as root, leaf, berry, flower, seed, etc. However, the above-described known effects are mainly those of ginseng root, i.e., the root part of ginseng, and researches on the parts other than ginseng root are insufficient.

Estrogen mediates various physiological phenomena by binding to estrogen receptors. Menopausal women experience various symptoms as the function of the reproductive organ ovary declines, with decreased secretion of the estrogen hormone and decreased activity of estrogen receptors. Representative menopausal symptoms comprise physical symptoms such as dizziness, sleep disorder, hot flashes, night sweats, etc. and psychological symptoms such as depression, fatigue, etc. Therefore, it can be seen that the regulation of the activity of estrogen receptors in women plays a very important role in the improvement and prevention of menopausal symptoms. Supplementation of estrogen is recommended around the menopause and medication is often necessary depending on the symptoms. However, since the previously known estrogen therapy is associated with increased risk of breast cancer due to increased growth and division of breast cancer cells as well as side effects such as endometritis, thromboembolism, hypertension, etc., development of natural product-derived functional health foods and drugs with few side effects on the human body is necessary.

SUMMARY OF THE INVENTION

In an aspect, the present disclosure is directed to providing a composition comprising a novel ginsenoside which has an effect of preventing or improving menopausal symptoms.

In an aspect, the present disclosure provides a composition for preventing or improving menopausal symptoms, which comprises (20S,24R)-6-O-β-D-glucopyranosyl (1→2)-β-D-glucopyranoside-dammar-3-one-20,24-epoxy-6a,12b,25-triol, a pharmaceutically acceptable salt thereof, a hydrate thereof or a solvate thereof as an active ingredient.

In an aspect, the present disclosure may provide a composition comprising a novel ginsenoside, a pharmaceutically acceptable salt thereof, a hydrate thereof or a solvate thereof, which has a superior effect in preventing or improving menopausal symptoms.

DETAILED DESCRIPTION OF THE PREFERRED EMBODIMENTS

Figure 1:
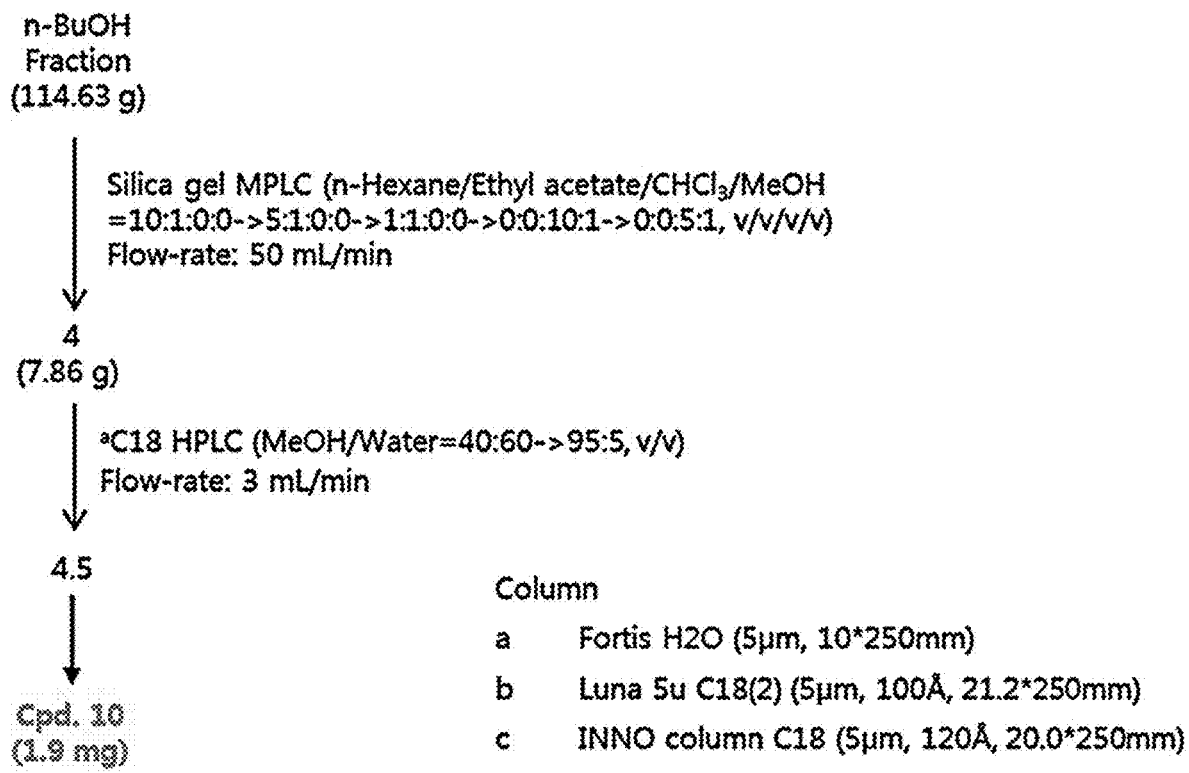
FIG. 1 shows a process of a separating a novel ginsenoside of the present disclosure (Compound 10) from compounds fractionated from a ginseng seed extract.
Figure 2A:
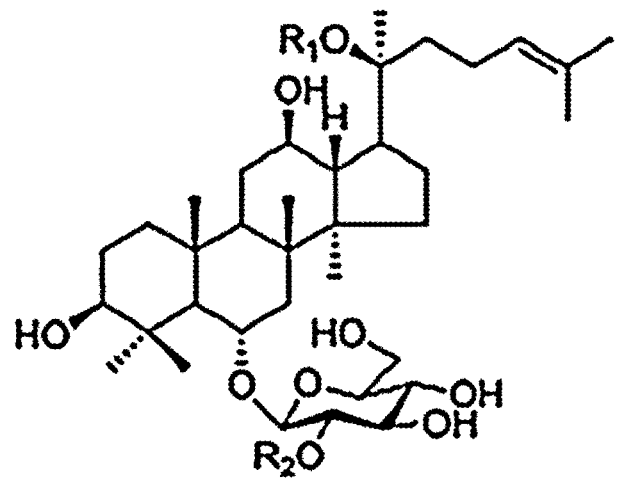
FIG. 2A shows the chemical structure of Compounds 1-3 fractionated from a ginseng seed extract.
Figure 2B:
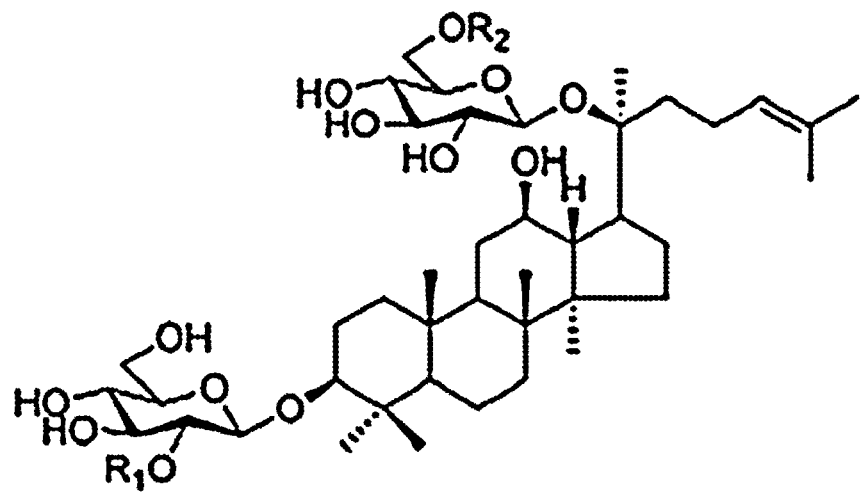
FIG. 2B shows the chemical structure of Compounds 4-6 fractionated from a ginseng seed extract.
Figure 2C:
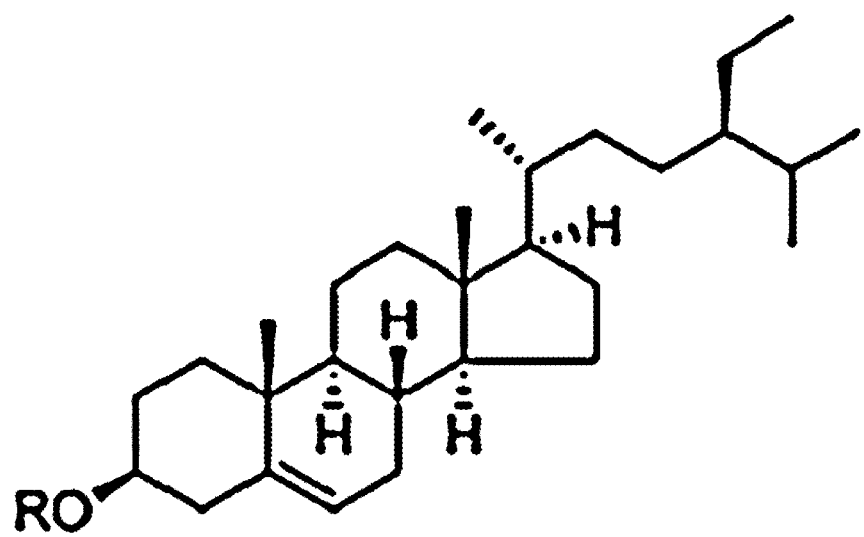
FIG. 2C shows the chemical structure of Compound 7 fractionated from a ginseng seed extract.
Figure 2D:
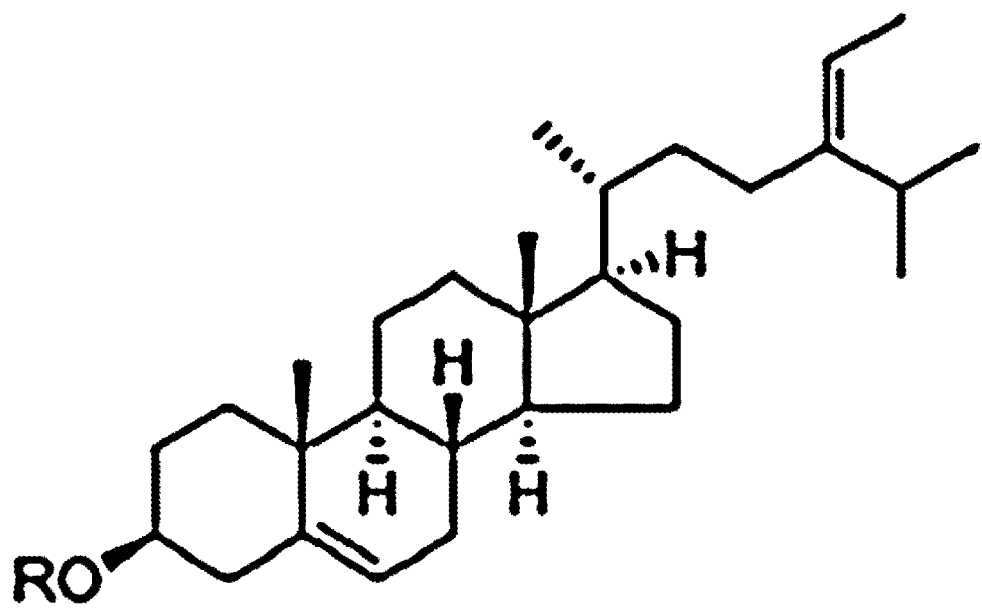
FIG. 2D shows the chemical structure of Compound 8 fractionated from a ginseng seed extract.
Figure 2E:
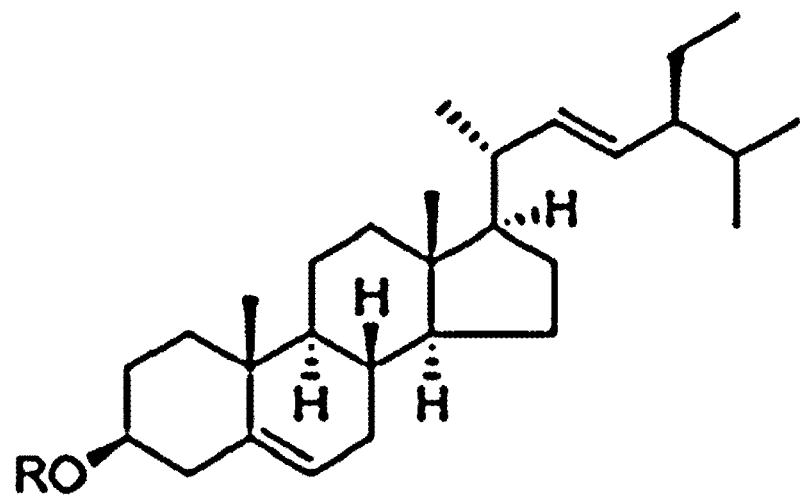
FIG. 2E shows the chemical structure of Compound 9 fractionated from a ginseng seed extract.
Figure 2F:
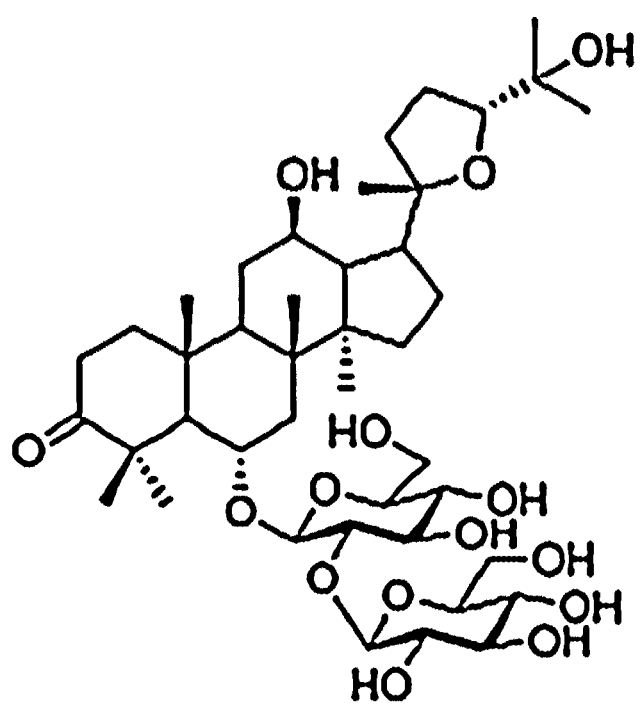
FIG. 2F shows the chemical structure of Compound 10 fractionated from a ginseng seed extract.
Figure 2G:
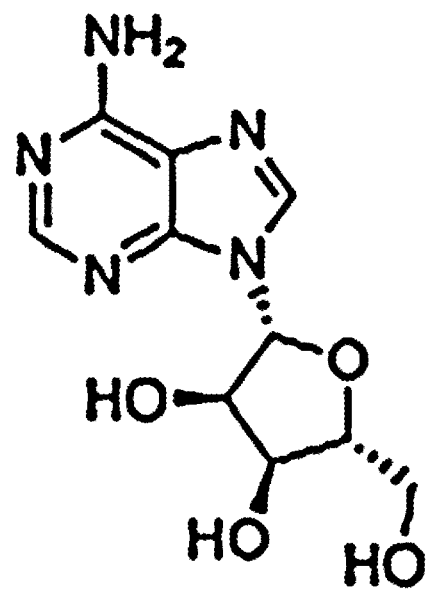
FIG. 2G shows the chemical structure of Compound 11 fractionated from a ginseng seed extract.
Figure 2H:
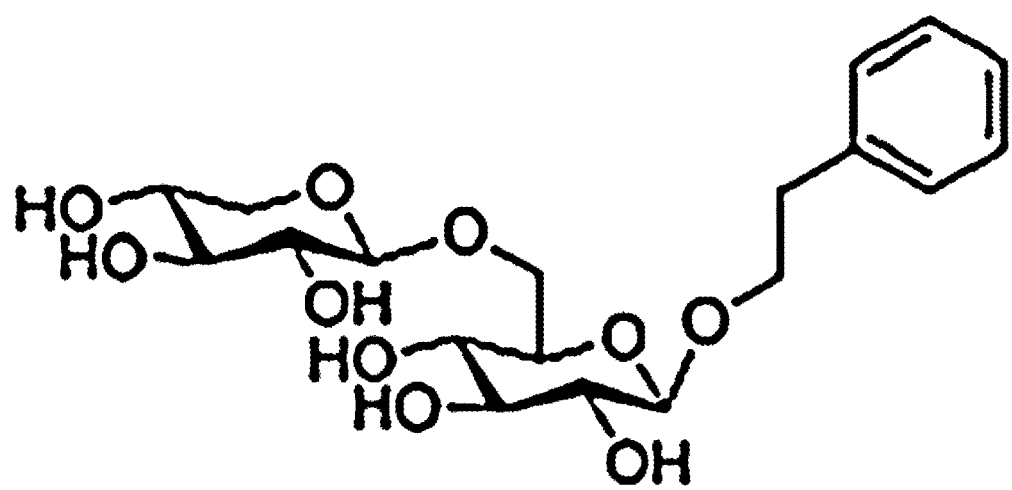
FIG. 2H shows the chemical structure of Compound 12 fractionated from a ginseng seed extract.
Figure 2I:
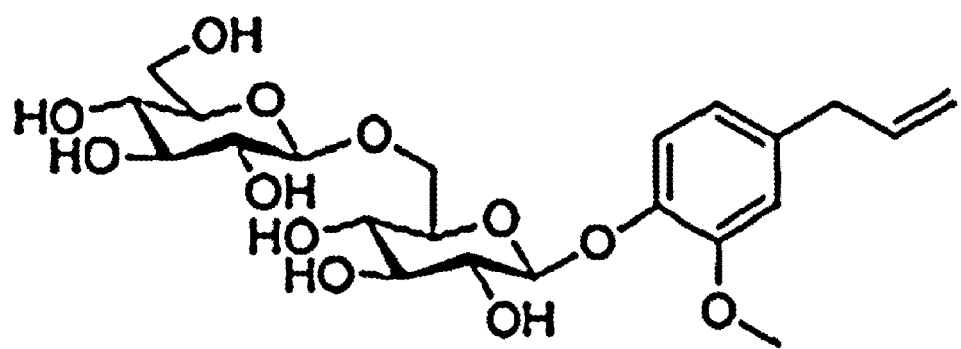
FIG. 2I shows the chemical structure of Compound 13 fractionated from a ginseng seed extract.
Figure 2J:
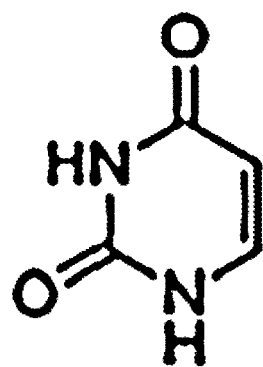
FIG. 2J shows the chemical structure of Compound 14 fractionated from a ginseng seed extract.
Figure 2K:
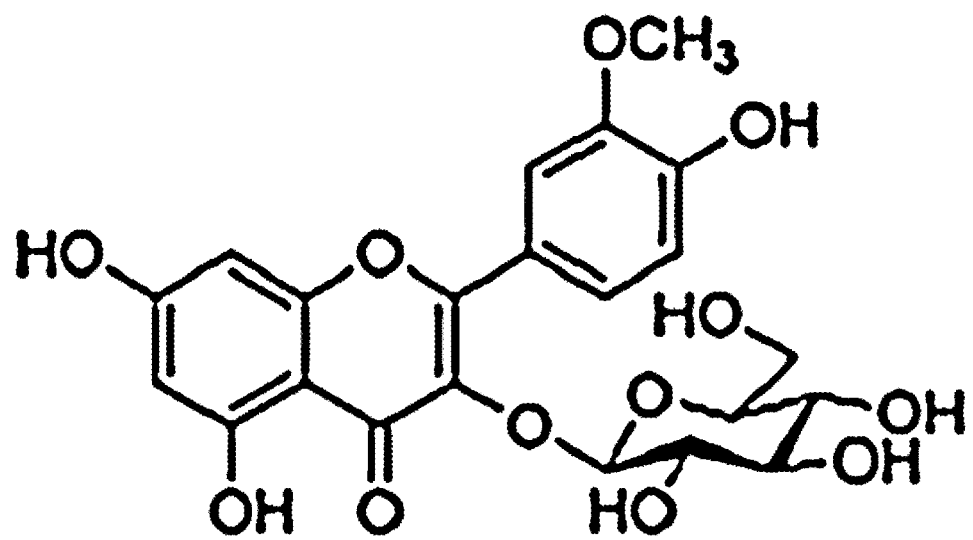
FIG. 2K shows the chemical structure of Compound 15 fractionated from a ginseng seed extract.
Figure 2L:
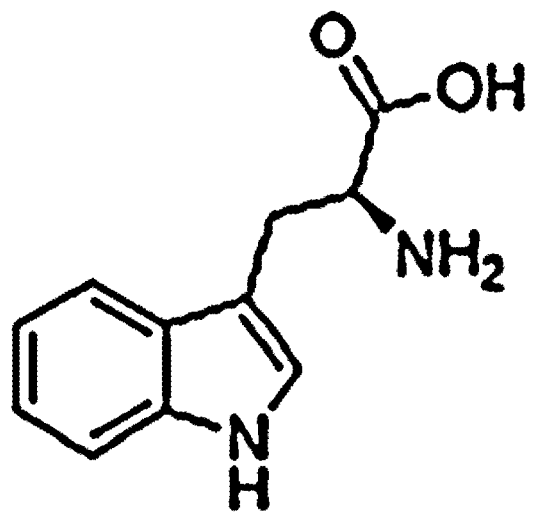
FIG. 2L shows the chemical structure of Compound 16 fractionated from a ginseng seed extract.
Figure 3A:
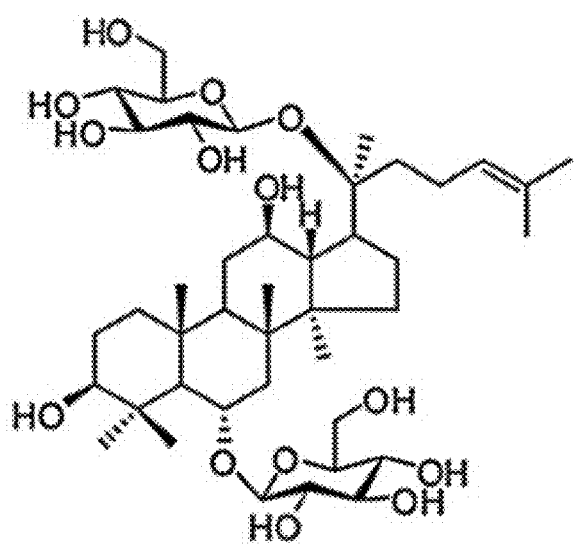
FIG. 3A shows the spectroscopic evidence and structure of Compound 1, which is a previously known ginsenoside fractionated from a ginseng seed extract.
Figure 3B:
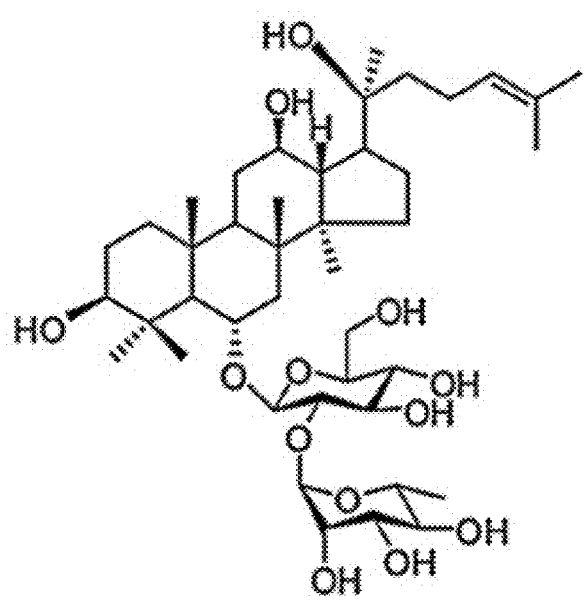
FIG. 3B shows the spectroscopic evidence and structure of Compound 2, which is a previously known ginsenoside fractionated from a ginseng seed extract.
Figure 3C:
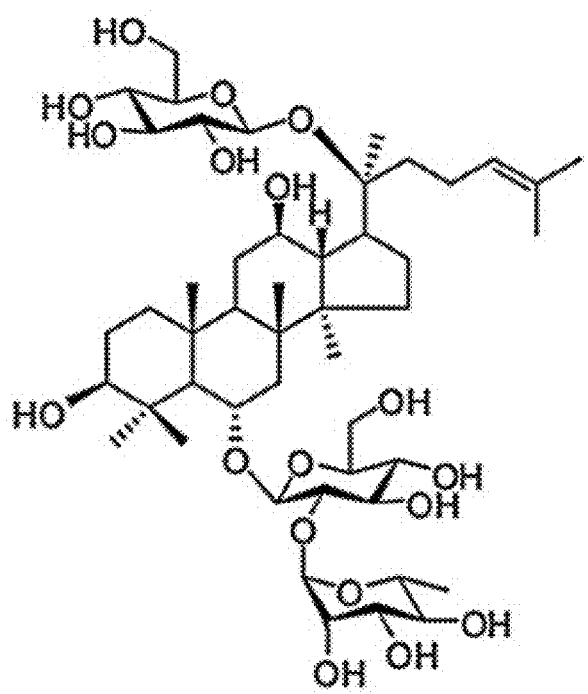
FIG. 3C shows the spectroscopic evidence and structure of Compound 3, which is a previously known ginsenoside fractionated from a ginseng seed extract.
Figure 3D:
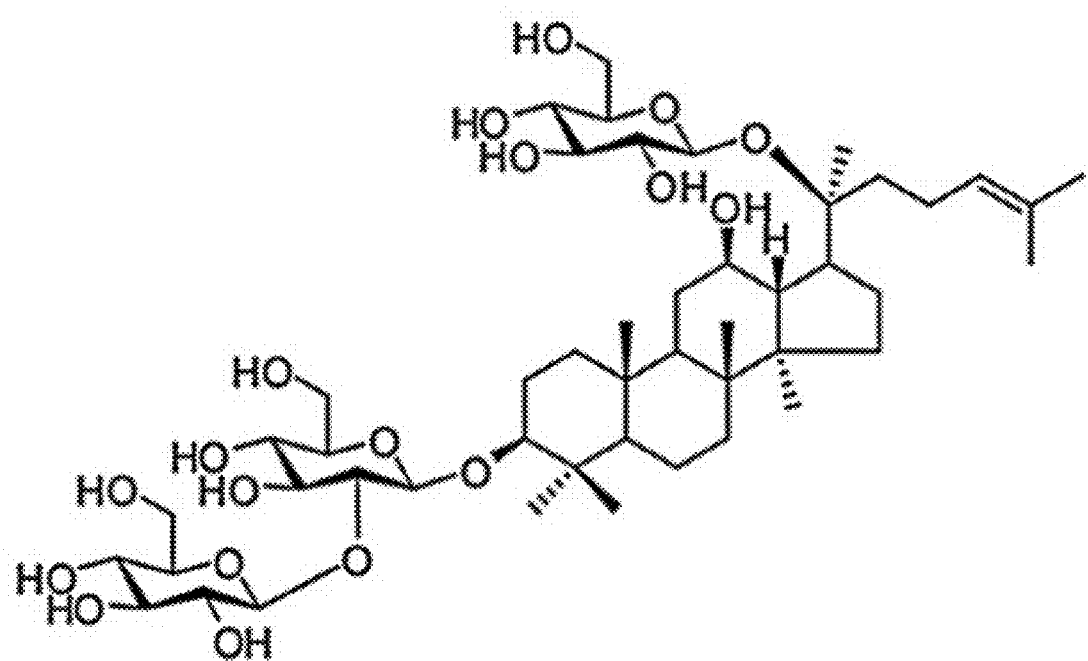
FIG. 3D shows the spectroscopic evidence and structure of Compound 4, which is a previously known ginsenoside fractionated from a ginseng seed extract.
Figure 3E:
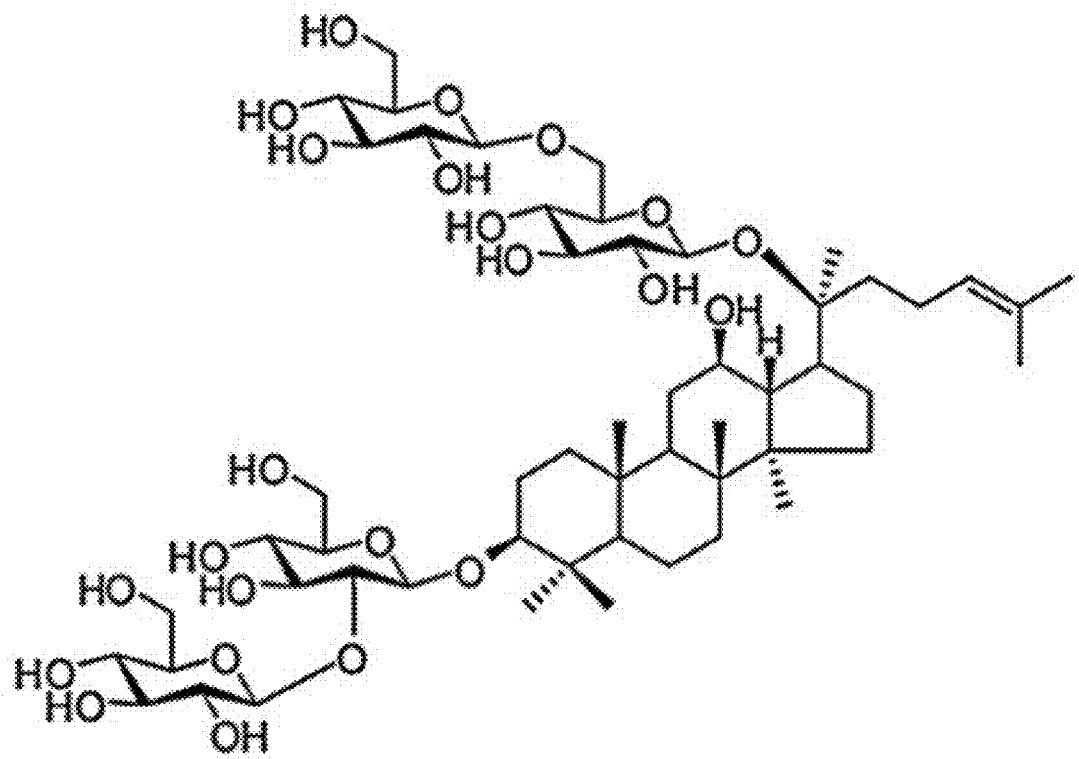
FIG. 3E shows the spectroscopic evidence and structure of Compound 5, which is a previously known ginsenoside fractionated from a ginseng seed extract.
Figure 3F:
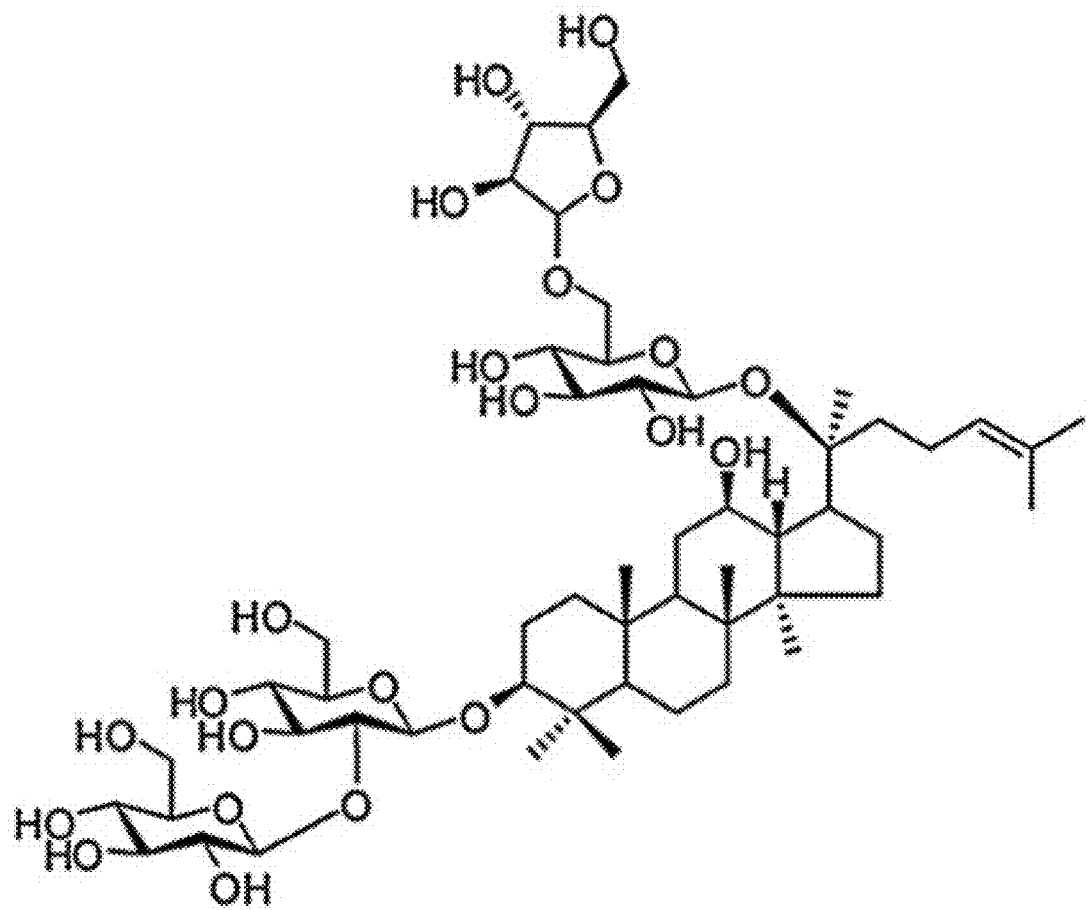
FIG. 3F shows the spectroscopic evidence and structure of Compound 6, which is a previously known ginsenoside fractionated from a ginseng seed extract.
Figure 4:
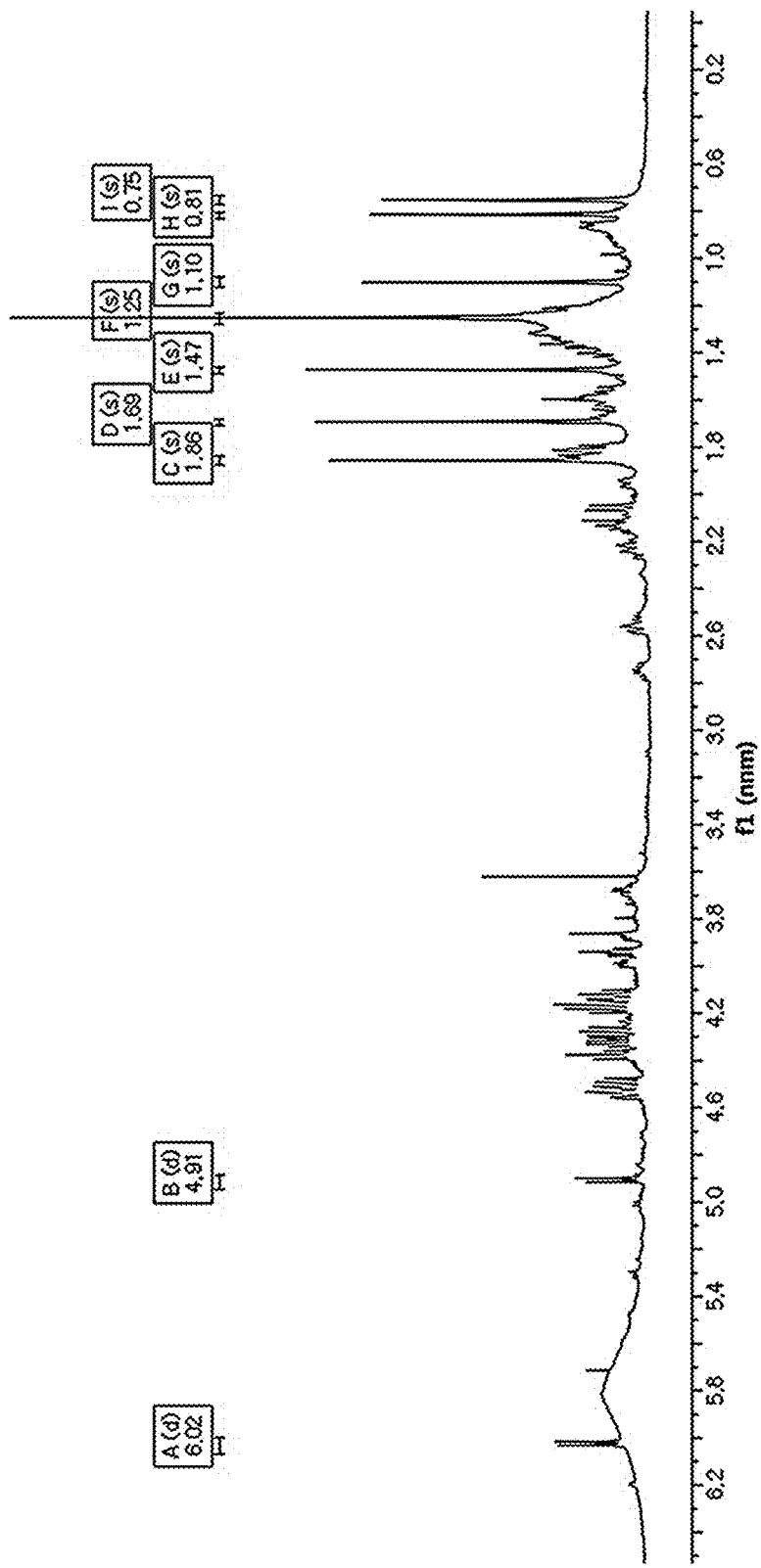
FIG. 4 shows the $^1$H-NMR spectrum of Compound 10, which is a novel ginsenoside of the present disclosure fractionated from a ginseng seed extract.
Figure 5:
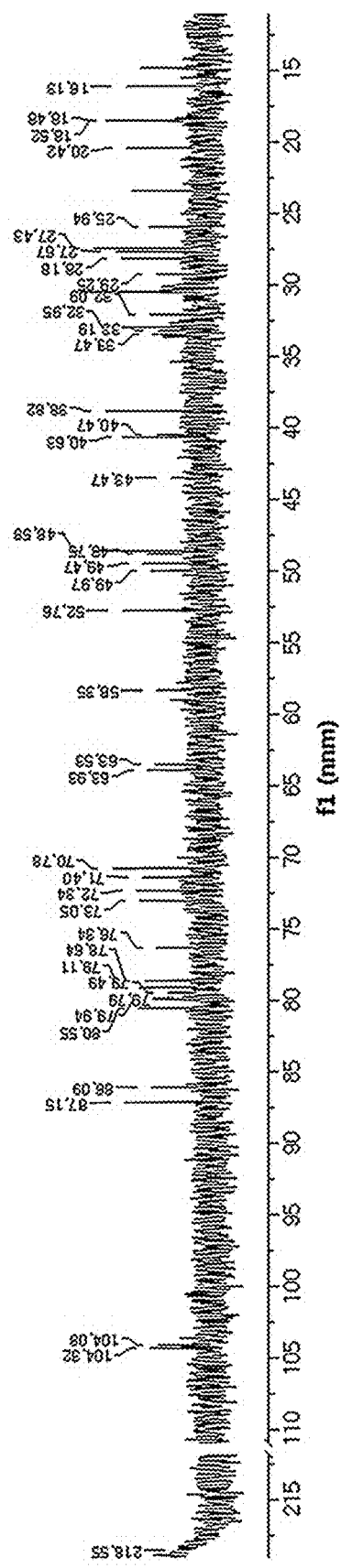
FIG. 5 shows the $^{13}$C-NMR spectrum of Compound 10, which is a novel ginsenoside of the present disclosure fractionated from a ginseng seed extract.
Figure 6:
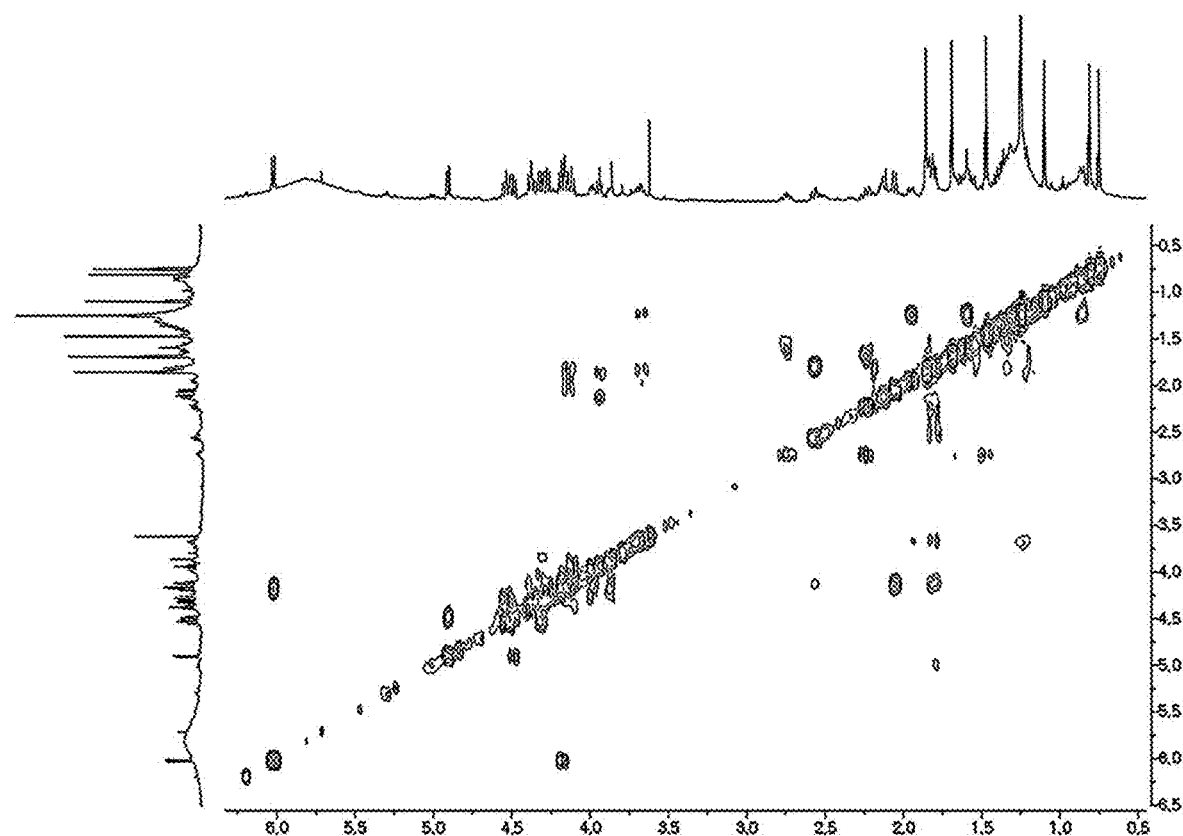
FIG. 6 shows the COSY spectrum of Compound 10, which is a novel ginsenoside of the present disclosure fractionated from a ginseng seed extract.
Figure 7:
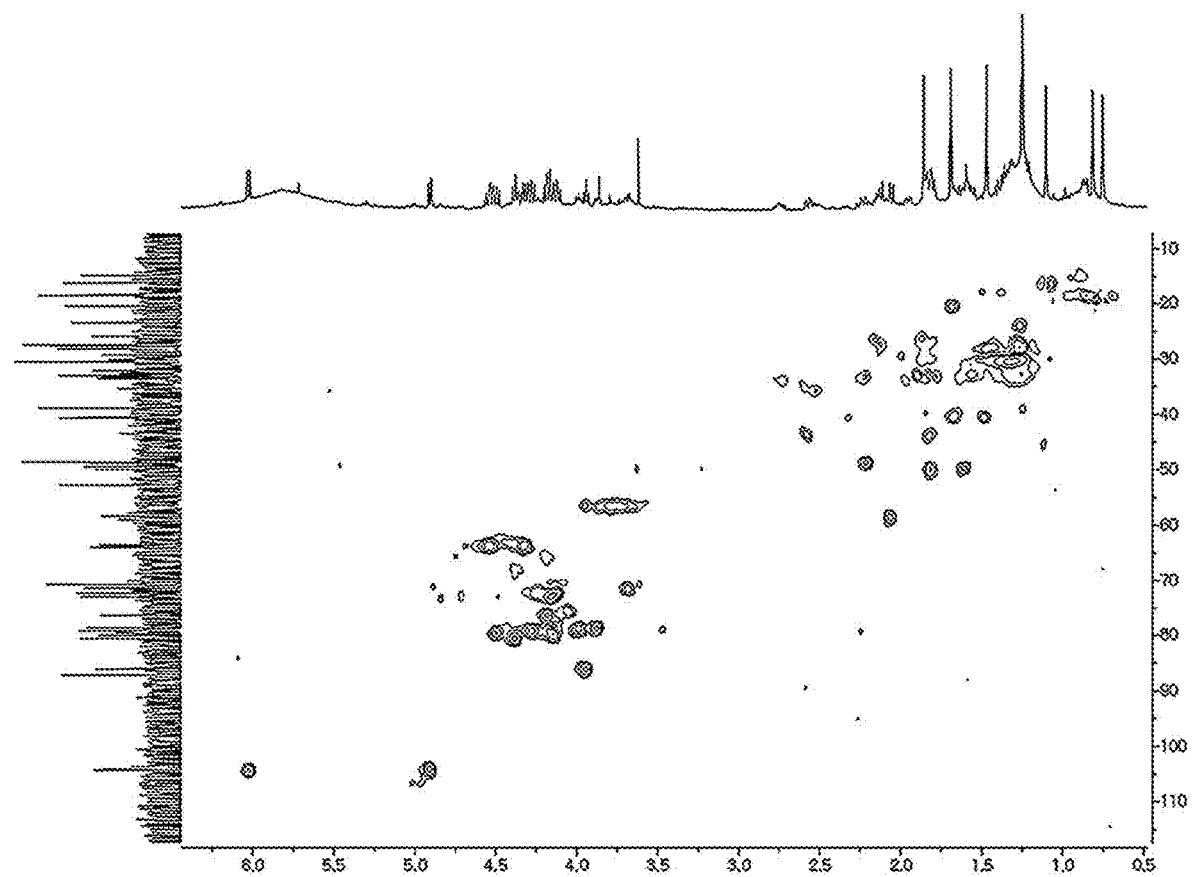
FIG. 7 shows the HSQC spectrum of Compound 10, which is a novel ginsenoside of the present disclosure fractionated from a ginseng seed extract.
Figure 8:
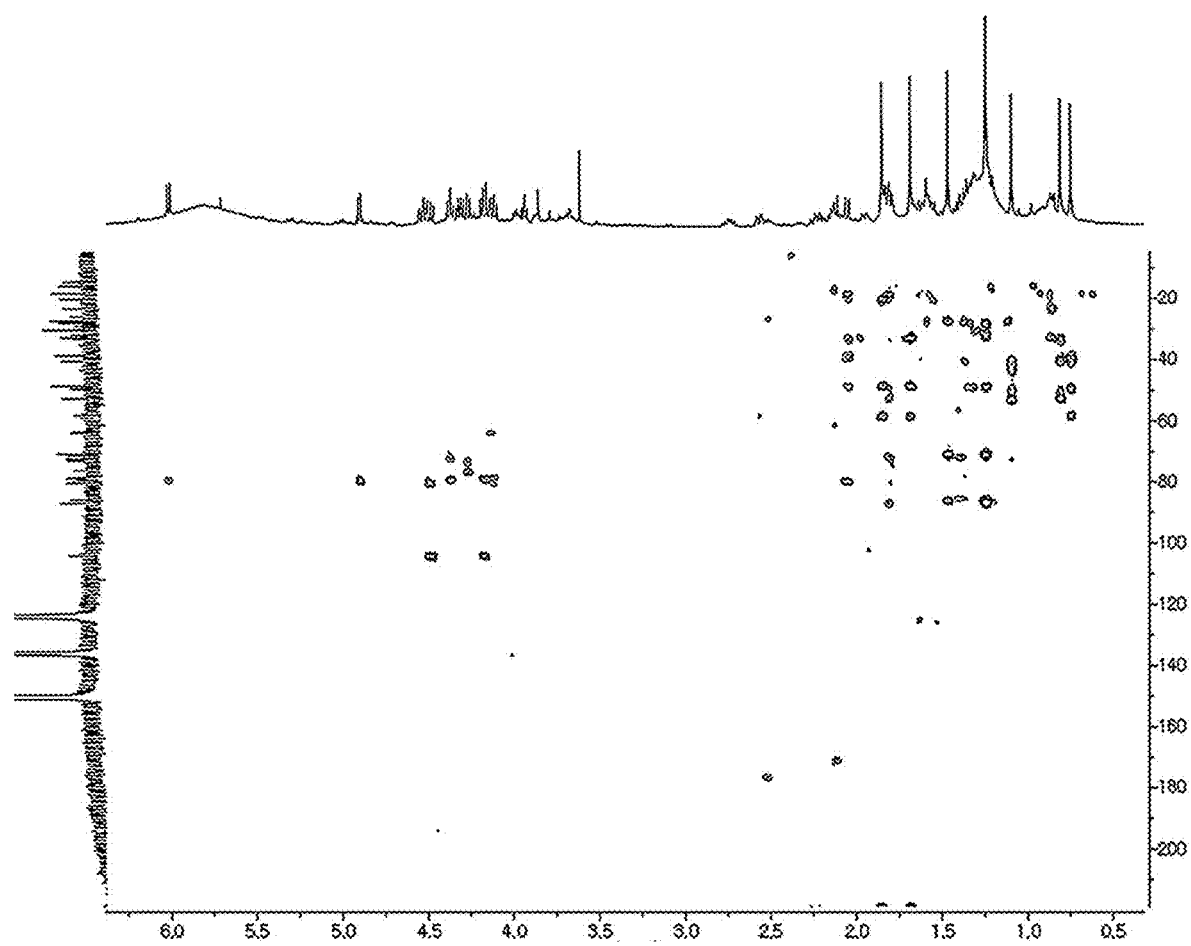
FIG. 8 shows the HMBC spectrum of Compound 10, which is a novel ginsenoside of the present disclosure fractionated from a ginseng seed extract.
Figure 9:
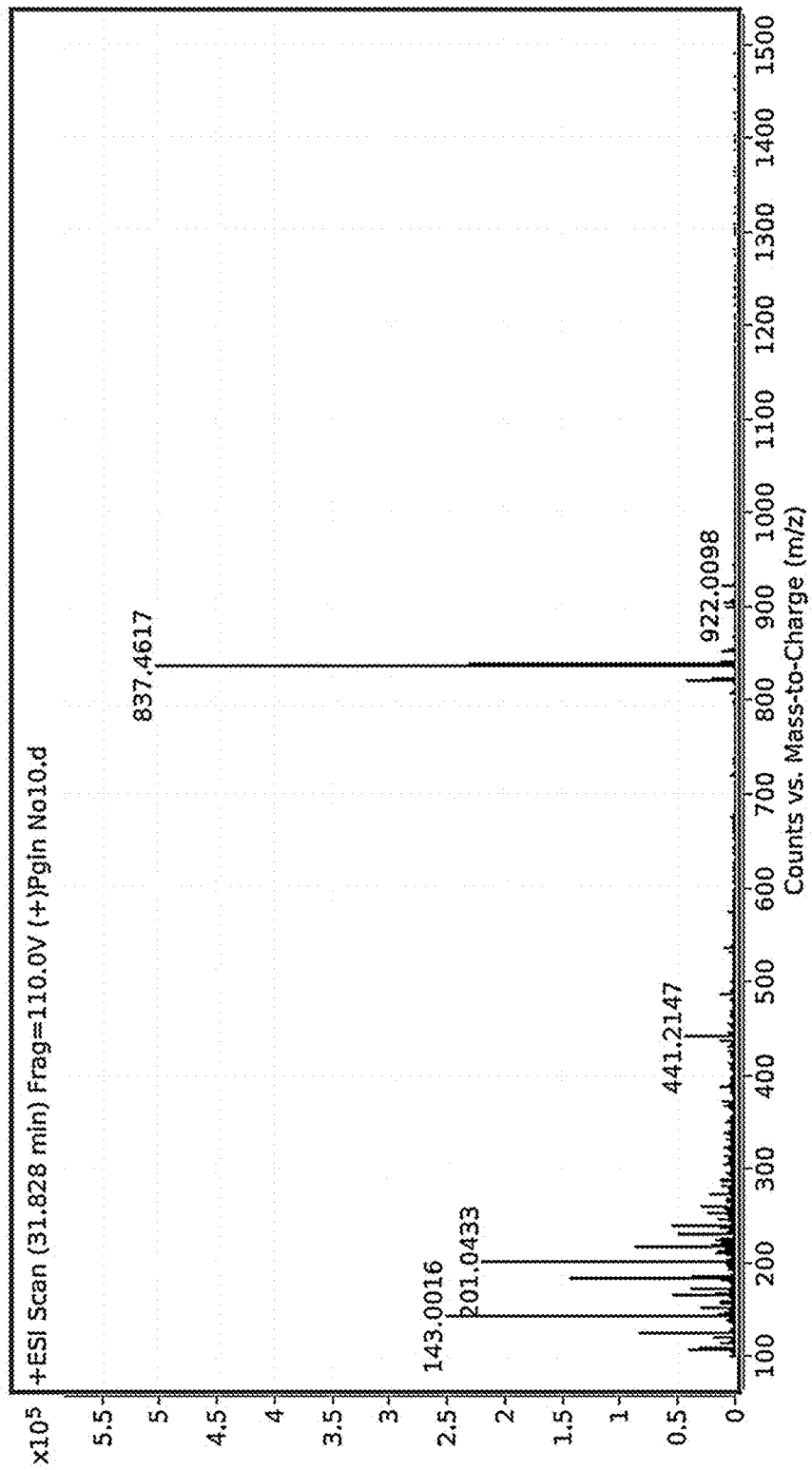
FIG. 9 shows the MS spectrum of Compound 10, which is a novel ginsenoside of the present disclosure fractionated from a ginseng seed extract.
Figure 10:
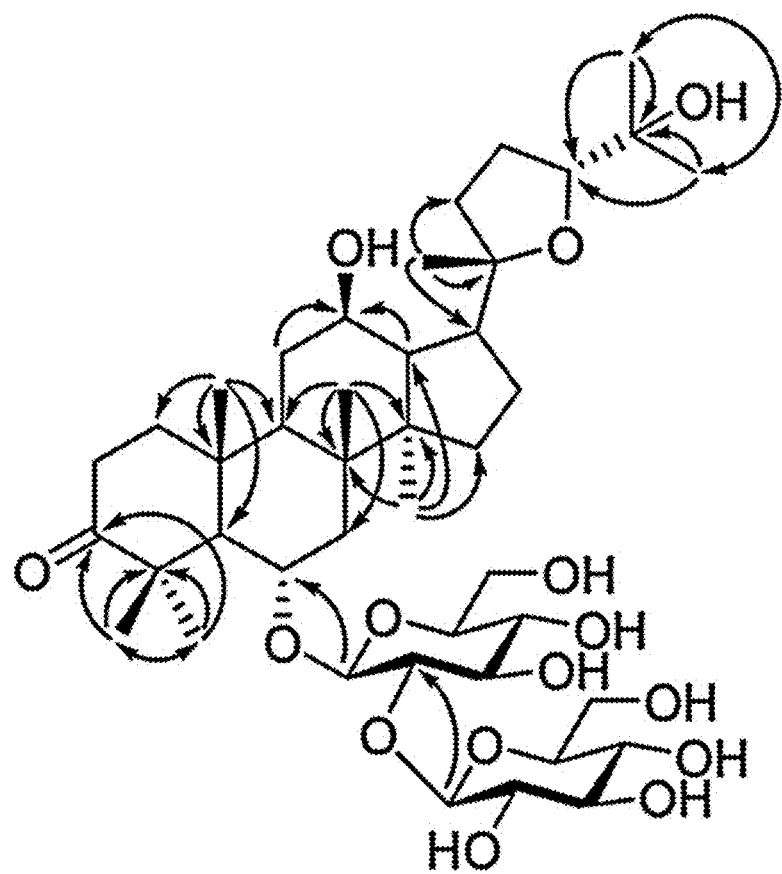
FIG. 10 shows the HMBC correlation of Compound 10, which is a novel ginsenoside of the present disclosure fractionated from a ginseng seed extract.

Hereinafter, the exemplary embodiments of the present disclosure will be described in more detail with reference to the accompanying drawings. However, the present disclosure is not limited to the exemplary embodiments described herein but may be embodied in other forms. Rather, the exemplary embodiments are provided so that this disclosure will be thorough and complete, and will fully convey the technical idea of the present disclosure to those skilled in the art. In the drawings, the width, thickness, etc. of elements are exaggerated for clarity. In addition, although only a part of an element is shown in some cases, those skilled in the art will easily understand the remaining part. In addition, those of ordinary skill in the art will be able to embody the technical idea of the present disclosure in various other forms within a range not departing from the technical idea of the present disclosure.

In an exemplary embodiment, the present disclosure may provide a composition for preventing or improving menopausal symptoms, which comprises a novel ginsenoside, a pharmaceutically acceptable salt thereof, a hydrate thereof or a solvate thereof as an active ingredient.

In an exemplary embodiment, the ginsenoside is (20S,24R)-6-O-β-D-glucopyranosyl(1→2)-β-D-glucopyranoside-dammar-3-one-20,24-epoxy-6a,12b,25-triol, which is a novel triterpene saponin.

In an exemplary embodiment, the present disclosure may provide a use of (20S,24R)-6-O-β-D-glucopyranosyl(1→2)-β-D-glucopyranoside-dammar-3-one-20,24-epoxy-6a,12b, 25-triol, a pharmaceutically acceptable salt thereof, a hydrate thereof or a solvate thereof for preparation of a composition for preventing or improving menopausal symptoms.

In an exemplary embodiment, the present disclosure may provide a method for preventing or improving menopausal symptoms, which comprises administering an effective amount of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof to a subject in need thereof.

In an exemplary embodiment, the present disclosure may provide (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof for use as an active ingredient of a composition for preventing or improving menopausal symptoms. In addition, the present disclosure may provide a non-therapeutic use of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof as an active ingredient for preventing or improving menopausal symptoms.

As used herein, the term "pharmaceutically acceptable" refers to those that can be approved or was approved by the government or equivalent regulatory agencies for use in animals, more specifically in humans, by avoiding significant toxic effects when used in conventional medicinal dosage, or those recognized as being listed in the pharmacopoeia or described in other general pharmacopoeia.

As used herein, the term "pharmaceutically acceptable salt" refers to a salt according to one aspect of the present disclosure that is pharmaceutically acceptable and possesses the desired pharmacological activity of the parent compound. The salts comprise (1) acid addition salts, formed with inorganic acids such as hydrochloric acid, hydrobromic acid, sulfuric acid, nitric acid, phosphoric acid, or the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, or the like; or (2) salts formed when an acidic proton present in the parent compound is substituted.

As used herein, a "hydrate" refers to a compound bound with water. It is used in a broad sense, comprising an inclusion compound which lacks chemical bonding with water.

As used herein, a "solvate" refers to a higher-order compound formed between a solute molecule or ion and a solvent molecule or ion.

In an exemplary embodiment, the ginsenoside has a molecular formula of $C_{42}H_{70}O_{15}$ and has the following chemical structure.

[Chemical Formula 1]

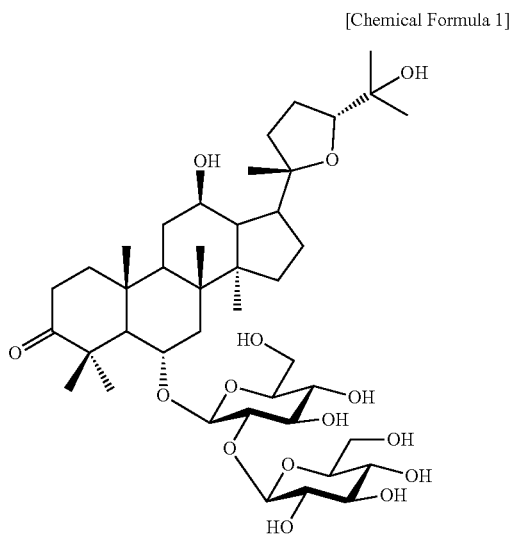

In the present disclosure, the novel ginsenoside is also referred to as "pseudoginsenoside $RT_8$" or "PG-$RT_8$".

In an exemplary embodiment, the ginsenoside may be extracted from ginseng seed. More specifically, the ginsenoside may be isolated from a ginseng seed extract, although not being limited thereto. In an exemplary embodiment, the ginseng may be *Panax ginseng* C.A. Meyer.

As used herein, "isolation" comprises extraction or fractionation from a ginseng seed extract, using water, an organic solvent, etc., by any method known to those skilled in the art. The fractionation may be performed after the extraction.

As used herein, the term "extract" means a substance obtained by extracting a component contained inside of a natural substance, regardless of the extracted method or ingredients. The term is used in a broad sense comprising, for example, all of those obtained by extracting a component soluble in a solvent from a natural substance using water or an organic solvent, extracting only a specific component of a natural substance, or the like.

As used herein, "fractions" comprise those obtained by fractionating a specific substance or extract using a certain solvent or those leftover after fractions, and extracting them again with a specific solvent. Fractional methods and extraction methods may be any method known to those skilled in the art.

In an exemplary embodiment, the ginsenoside may be one isolated from a methanol- and butanol-soluble extract of ginseng seed. Specifically, the ginsenoside may be detected and isolated from a methanol- and butanol-soluble extract of ginseng seed by HPLC-ESI-Q-TOF-MS. Because the main ingredients of the ginseng seed extract are lipids, not all triterpene and steroid saponins can be observed from a crude ginseng seed extract by HPLC-UV or HPLC-ELSD.

As used herein, the term "menopausal symptom" means physical or psychological changes and symptoms occurring with decreased secretion of the estrogen hormone or decreased activity of the estrogen receptors. In an exemplary embodiment, the menopausal symptoms may comprise climacteric symptoms. For example, the menopausal symptoms may comprise one or more physical or psychological symptoms comprising dizziness, sleep disorder, hot flashes, osteoporosis, night sweats, depression, headache and fatigue.

As used herein, the term "prevention" refers to any action of inhibiting or delaying the target symptoms by administering the composition according to an exemplary embodiment of the present disclosure. As used herein, the term "treatment" refers to any action of improving or alleviating the target symptoms by administering the composition according to an exemplary embodiment of the present disclosure. As used herein, the term "improvement" refers to any action of improving or favorably changing the target symptoms by administering the composition according to an exemplary embodiment of the present disclosure.

The composition according to an exemplary embodiment of the present disclosure may increase the activity of the estrogen receptors ERα (estrogen receptor α) and ERβ (estrogen receptor β). Although menopausal symptoms may be alleviated by increasing the activity of the estrogen receptors ERα and ERμ, ERβ may be more suitable as a molecular target for safely improving menopausal symptoms than ERα. Deroo B J et al., J Clin Invest 116:561 (2006), which is incorporated herein by reference in its entirety, reported that ERα is overexpressed in most breast cancer cells, which is manifested mainly by increased ERα. The ESR1 described in the literature, which is increased in cancers, is ERα. In addition, Harris H A et al., Evaluation of an estrogen receptor-beta agonist in animal models of human disease, *Endocrinology* 144:4241 (2003), which is incorporated herein by reference in its entirety, reported that the decrease in ERβ also affects colon cancer. The composition according to an exemplary embodiment of the present disclosure exhibits a high ratio of activity for Erβ as compared to ERα and, thus, can effectively prevent or improve menopausal symptoms by improving the side effects of existing products for improving menopausal symptoms, such as the risk of breast cancer. In an exemplary embodiment, when the composition is administered to a subject, the ratio of the activity of the estrogen receptors Erβ to ERα may be 1.1 times or greater, specifically 1.1 times or greater and 3 times or smaller, although not being limited thereto. More specifically, the ratio of the activity of Erβ to ERα may be 1.1 times or greater, 1.2 times or greater, 1.3 times or greater, 1.4 times or greater, 1.5 times or greater, 1.6 times or greater, 1.7 times or greater, 1.8 times or greater, 1.9 times or greater, 2 times or greater, 2.1 times or greater, 2.2 times or greater, 2.3 times or greater, 2.4 times or greater or 2.5 times or greater, and 3 times or smaller, 2.9 times or smaller, 2.8 times or smaller, 2.7 times or smaller, 2.6 times or smaller, 2.5 times or smaller, 2.4 times or smaller, 2.3 times or smaller, 2.2 times or smaller, 2.1 times or smaller or 2 times or smaller.

In an exemplary embodiment, the active ingredient may be comprised in an amount of 0.0001-99.9 wt % based on the total weight of the composition. Specifically, in an exemplary embodiment, the composition may comprise the active ingredient in an amount of 0.0001 wt % or more, 0.0005 wt % or more, 0.001 wt % or more, 0.01 wt % or more, 0.1 wt % or more, 1 wt % or more, 2 wt % or more, 3 wt % or more, 4 wt % or more, 5 wt % or more, 6 wt % or more, 7 wt % or more, 8 wt % or more, 9 wt % or more, 10 wt % or more, 15 wt % or more, 20 wt % or more, 25 wt % or more, 30 wt % or more, 35 wt % or more, 40 wt % or more, 45 wt % or more, 50 wt % or more, 55 wt % or more, 60 wt % or more, 65 wt % or more, 70 wt % or more, 75 wt % or more, 80 wt % or more, 85 wt % or more, 90 wt % or more, 95 wt % or more or 99.9 wt % or more, based on the total weight of the composition, although not being limited thereto. Alternatively, in an exemplary embodiment, the composition may comprise the active ingredient in an amount of 100 wt % or less, 99 wt % or less, 95 wt % or less, 90 wt % or less, 85 wt % or less, 80 wt % or less, 75 wt % or less, 70 wt % or less, 65 wt % or less, 60 wt % or less, 55 wt % or less, 50 wt % or less, 45 wt % or less, 40 wt % or less, 35 wt % or less, 30 wt % or less, 25 wt % or less, 20 wt % or less, 15 wt % or less, 10 wt % or less, 9 wt % or less, 8 wt % or less, 7 wt % or less, 6 wt % or less, 5 wt % or less, 4 wt % or less, 3 wt % or less, 2 wt % or less, 1 wt % or less, 0.5 wt % or less, 0.1 wt % or less, 0.01 wt % or less, 0.001 wt % or less or 0.0005 wt % or less, based on the total weight of the composition, although not being limited thereto.

The composition according to exemplary embodiments of the present disclosure may be a food composition comprising the active ingredient.

For example, the composition may be processed into a functional food comprising the active ingredient, such as fermented milk, cheese, yogurt, juice, a probiotic, a health food, etc. and may also be used in the form of various food additives. In an exemplary embodiment, the composition may be a health food composition. In an exemplary embodiment, the health food composition may be formulated as a pill, a capsule, a tablet, a granule, a caramel, a drink, etc. In another exemplary embodiment, it may be processed into such forms as a liquid, a powder, a granule, a tablet, a tea bag, etc. The composition may be administered by various methods such as simple drinking, administration by injection, spraying, squeezing, etc. The composition may comprise other ingredients, etc. that may provide a synergistic effect to a main effect within a range not negatively affecting the main effect of the present disclosure. For example, it may further comprise an additive such as a flavorant, a colorant, a sterilizer, an antioxidant, an antiseptic, a moisturizer, a thickener, a mineral, an emulsifier, a synthetic polymer, etc. for improvement of physical properties. In addition, it may further comprise an auxiliary ingredient such as a water-soluble vitamin, an oil-soluble vitamin, a polypeptide, a polysaccharide, a seaweed extract, etc. These ingredients may be selected and mixed adequately by those skilled in the art depending on the formulation or purpose of use, and the addition amount thereof may be selected within ranges not negatively affecting the purpose and effect of the present disclosure. For example, the addition amount of these ingredients may be 0.0001-99.9 wt % based on the total weight of the composition. In an exemplary embodiment, the administration amount of the food composition may vary depending on the age, sex and body weight of the subject, the particular disease or pathological condition of the subject, the severity of the disease or pathological condition, administration route, etc., and the determination of the administration amount based on these factors is within the level of those skilled in the art. For example, the administration amount may be 0.05 mg/kg/day or more or 1 mg/kg/day or more, and 10 g/kg/day or less, 100 mg/kg/day or less or 10 mg/kg/day or less. However, the administration amount does not limit the scope of the present disclosure by any means.

The composition according to exemplary embodiments of the present disclosure may be a pharmaceutical composition comprising the active ingredient. The pharmaceutical composition may further comprise a pharmaceutical adjuvant such as an antiseptic, a stabilizer, a wetting agent, an emulsification accelerator, a salt and/or buffer for adjusting osmotic pressure, etc. and other therapeutically useful materials.

In an exemplary embodiment, the pharmaceutical composition may be a composition for oral administration. For example, the composition for oral administration may be a tablet, a pill, a hard or soft capsule, a liquid, a suspension, an emulsion, a syrup, a powder, a dust, a fine granule, a granule, a pellet, etc. These formulations may further comprise, in addition to the active ingredient, a surfactant, a diluent (e.g., lactose, dextrose, sucrose, mannitol, sorbitol, cellulose and glycine) and a lubricant (e.g., silica, talc, stearic acid and its magnesium or calcium salts, and polyethylene glycol). A tablet may further comprise a binder such as magnesium aluminum silicate, starch paste, gelatin, tragacanth, methyl cellulose, sodium carboxymethyl cellulose or polyvinylpyrrolidone. If necessary, the tablet may further comprise other pharmaceutical additives, for example, a disintegrant such as starch, agar, alginic acid or a sodium salt thereof, an adsorbent, a coloring agent, a flavorant, a sweetener, etc. The tablet may be prepared by a common mixing, granulation or coating method.

In an exemplary embodiment, the pharmaceutical composition may be a composition for parenteral administration, and the composition for parenteral administration may be a formulation for rectal, topical, subcutaneous or transdermal administration. For example, the formulation may be an injection, a medicinal drop, an ointment, a lotion, a gel, a cream, a spray, a suspension, an emulsion, a suppository, a patch, etc., although not being limited thereto.

In an exemplary embodiment, the administration amount of the pharmaceutical composition will vary depending on the age, sex and body weight of the subject to be treated, the particular disease or pathological condition to be treated, the severity of the disease or pathological condition, and the discretion of a prescriber. The determination of the administration amount based on these factors is within the level of those skilled in the art. For example, the administration amount may be 0.05 mg/kg/day or more or 1 mg/kg/day or more, and 10 g/kg/day or less, 100 mg/kg/day or less or 10 mg/kg/day or less. However, the administration amount does not limit the scope of the present disclosure by any means.

Hereinafter, the present disclosure will be described in detail referring to examples, comparative examples and test examples. However, the following examples are for illustrative purposes only and it will be obvious to those or ordinary skill in the art that the scope of the present disclosure is not limited by the examples, comparative examples and test examples.

All the experimental values given below are averages of at least three repeated experiments and standard deviation (SD) is represented by error bars. p values were calculated by one-way ANOVA and Dunnett's test, and p values smaller than 0.05 were considered statistically significant.

[Example 1] Isolation of Ginsenosides

Fractionation 5.5 kg of Ginseng seed (seeds of Panax ginseng) was finely ground with a mixer to make a powder form, which was extracted with methanol and then fractionated step by step using n-hexane, ethyl acetate, n-butanol, etc. Lipids were mostly removed by n-hexane, and the lipids remaining in the ethyl acetate fraction were suspended in methanol: water (=1:1 (v/v)), stored in a freezer overnight, and then only the supernatant was taken. The lipids were removed once more using a centrifuge. 2.61 g of the ethyl acetate fraction and 114.64 g of the n-butanol fraction thus pretreated were fractionated through column and high-performance counter-current chromatography (HPCCC) as follows.

Fractionation of n-Butanol Fraction Using Column and HPCCC 114.64 g of the n-butanol fraction was fractionated by MPLC. n-Hexane/ethyl acetate (=10:1→5:1→1:1) and $CHCl_3$/MeOH (=10:1→5:1 (v/v)) were used as solvents and the flow rate was 50 mL/min. A total of 12 subfractions were obtained under the above conditions, and the components comprised in each fraction were separated again using HPCCC, high-performance liquid chromatography (HPLC), Sephadex LH-20 column, etc. 16 compounds were identified by investigating their structure using nuclear magnetic resonance (NMR), ultraviolet (UV) spectroscopy and mass spectrometry (MS).

The isolated 16 compounds comprise: ginsenoside Rg1 (Compound 1), ginsenoside Rg2 (Compound 2) and ginsenoside Re (Compound 3), which are protopanaxatriol saponins; ginsenoside Rd (Compound 4), ginsenoside Rb1 (Compound 5) and ginsenoside Rb2 (Compound 6), which are protopanaxadiol saponins; stigma-5-en-3-O-β-D-glucopyranoside (Compound 7), stigma-5,24(28)-dien-3-O-β-D-glucopyranoside (Compound 8) and stigma-5,22-dien-3-O-β-D-glucopyranoside (Compound 9), which are sterol glycosides; (20S,24R)-6-O-β-D-glucopyranosyl(1→2)-β-D-glucopyranoside-dammar-3-one-20,24-epoxy-6a,12b,25-triol (Compound 10), which is a novel ginsenoside compound according to an exemplary embodiment of the present disclosure first isolated from a natural product; phenethyl alcohol β-D-xylopyranosyl(1→6)-β-D-glucopyranoside) (Compound 12) and eugenyl β-gentiobioside (Compound 13), which are phenolic glycosides; isorhamnetin 3-O-β-D-glucopyranoside (Compound 15), which is a flavonoid; and adenosine (Compound 11), uracil (Compound 14) and tryptophan (Compound 16), which are primary metabolites.

The isolation process of Compound 10, which is a novel ginsenoside according to an embodiment of the present disclosure, is shown in FIG. 1. The chemical structures of the 16 compounds are shown in FIGS. 2A-2L, and the spectroscopic evidence and chemical structures of the previously known ginsenosides (Compounds 1-6) among the above compounds are additionally shown in FIGS. 3A-3F.

Compound 10 was isolated as a white amorphous powder with the molecular formula $C_{42}H_{70}O_{15}$ based on the sodiated pseudomolecular ion peak at m/z 837.4617 [(M+Na)+ calcd. 837.4612] in the cationic electrospray ionization-quadrupole-time-of-flight mass spectrometry (ESI-Q-TOF-MS) spectrum. The $^1$H NMR spectrum of Compound 10 comprises 8 methyl resonance peaks [$\delta_H$ 1.86 (3H, s, H-28), 1.69 (3H, s, H-29), 1.47 (3H, s, H-27), 1.25 (6H, s, H-21, 26), 1.10 (3H, s, H-18), 0.81 (3H, s, H-30), 0.75 (3H, s, H-19)]. In addition, two pairs of signals corresponding to anomeric protons and carbon atoms at two sugar residues were detected at $\delta_H$ 6.02 (1H, d, J=7.8, H-2")/$\delta_C$ 104.08 (C-1') and $\delta_H$ 4.91 (1H, d, J=7.7, H-1')/$\delta_C$ 104.32 (C-1"). The $^{13}$C NMR and heteronuclear single quantum correlation (HSQC) spectra revealed 42 carbon signals. Apart from the above two sugar residues, the aglycone of Compound 10 had eight methylenes, four methines, three oxygen-containing methines [$\delta_C$ 79.79 (C-6), 71.40 (C-12) and 86.09 (C-24)], five quaternary carbon atoms, two oxygenated quaternary carbon atoms [$\delta_C$ 87.15 (C-20) and 70.78 (C-25)], eight methyl groups and carbonyl carbon [$\delta_C$ 218.85 (C-3)]. As a result of thorough interpretation of the $^1$H and $^{13}$C NMR data, the aglycone of Compound 10 was found to be superimposed on pseudoginsengenin R1 [(20S,24R)-dammar-3-one-20,24-epoxy-6α,12β,25-triol])]. The absolute configuration of C-20 in Compound 10 was deduced from S to chemical shift of C-21 ($\delta_C$ 27.67), and the 24R configuration was determined by chemical shift of C-24 ($\delta_C$ 86.09) as previously published. Both sugar units were turned out to be β-D-glucopyranosyl residues from the coupling constants of the anomeric protons in the $^1$H NMR spectra and 12 carbon resonances, together with acid hydrolysis data and gas chromatography (GC) analysis results. A glycoside linkage was determined by heteronuclear multiple bond correlation (HMBC) which showed cross peaks at $\delta_H$ 6.02 (H-1")/$\delta_C$ 79.49 (C-2') and $\delta_H$ 4.91 (H-1')/$\delta_C$ 79.79 (C-6), and it was demonstrated that 2-O-(β-D-glucopyranosyl-β-D-glucopyranosyl residues were linked to C-6 of aglycone at pseudoginsengenin R1. Each of the analytical spectra of Compound 10 and the core HBMC correlation are shown in FIGS. 4 to 10.

As a result of the analysis, the chemical structure of Compound 10 was determined as (20S,24R)-6-O-β-D-glucopyranosyl(1→2)-β-D-glucopyranoside-dammar-3-one-20,24-epoxy-6a,12b,25-triol, and the compound was named pseudoginsenoside RT8 (PG-RT$_8$).

Among the ginsenosides isolated from the ginseng seed extract, ginsenoside Rg1 (Compound 1), ginsenoside Rg2 (Compound 2) and ginsenoside Re (Compound 3), which are protopanaxtriol (PPT)-based ginsenosides, comprise three hydroxyl groups in the ginsenoside backbone. Ginsenoside Rd (Compound 4), ginsenoside Rb1 (Compound 5) and ginsenoside Rb2 (Compound 6), which are protopanaxdiol (PPD)-based ginsenosides, comprise two hydroxyl groups in the ginsenoside backbone. On the other hand, Compound 10, which is a ginsenoside newly isolated and identified in the present disclosure, has a PPT-based backbone, but the terminal hydroxyl group of the backbone is a ketone, and there is a structural difference in that the linear chain of the ginsenoside is cyclized into a furan ring.

Compound 10, which was newly isolated and identified in the present disclosure, had a molecular formula of $C_{42}H_{70}O_{15}$. ESI-Q-TOF-MS m/z was 837.4617 [M+Na]+ and the $^1$H- and $^{13}$C-NMR spectra data are given in the following tables.

TABLE 1

| Position | 13C-NMR | 1H-NMR |
|---|---|---|
| 1 | 40.63 | 1.67 (1H, H-1a)$^a$, 1.49 (1H, H-1b)$^a$ |
| 2 | 33.61 | 2.23 (1H, H-2a)$^a$, 1.78 (1H, H-2b)$^a$ |
| 3 | 218.85 | — |
| 4 | 48.58 | — |

TABLE 1-continued

| Position | 13C-NMR | 1H-NMR |
|---|---|---|
| 5 | 58.35 | 2.06 (1H, d, J = 10.6 Hz, H-5) |
| 6 | 79.79 | 4.15 (1H, H-6)$^a$ |
| 7 | 43.47 | 2.57 (1H, H-7a)$^a$, 1.82 (1H, H-7b)$^a$ |
| 8 | 40.47 | — |
| 9 | 49.47 | 1.60 (1H, H-9)$^a$ |
| 10 | 38.82 | — |
| 11 | 33.47 | 2.22 (1H, H-11a)$^a$, 1.32 (1H, H-11b)$^a$ |
| 12 | 71.40 | 3.68 (1H, td, J = 10.6, 4.5 Hz, H-12) |
| 13 | 49.97 | 1.81 (1H, H-13)$^a$ |
| 14 | 52.76 | — |
| 15 | 33.19 | 1.64 (1H, H-15a)$^a$, 1.26 (1H, H-15b)$^a$ |
| 16 | 25.94 | 2.17 (1H, H-16a)$^a$, 1.87 (1H, H-16b)$^a$ |
| 17 | 48.75 | 2.21 (1H, H-17)$^a$ |
| 18 | 16.13 | 1.10 (3H, s, H-18) |
| 19 | 18.48 | 0.75 (3H, s, H-19) |
| 20 | 87.15 | — |
| 21 | 27.67 | 1.25 (3H, s, H-21) |
| 22 | 32.09 | 1.60 (1H, H-22a)$^a$, 1.37 (1H, H-22b)$^a$ |
| 23 | 29.25 | 1.82 (1H, H-23a)$^a$, 1.25 (1H, H-23b)$^a$ |
| 24 | 86.09 | 3.94 (1H, t, J = 7.5 Hz, H-24) |
| 25 | 70.78 | — |
| 26 | 27.43 | 1.25 (3H, s, H-26) |
| 27 | 28.18 | 1.45 (3H, s, H-27) |
| 28 | 32.95 | 1.86 (3H, s, H-28) |
| 29 | 20.42 | 1.69 (3H, s, H-29) |
| 30 | 18.52 | 0.81 (3H, s, H-30) |

$^a$peak was overlapped

TABLE 2

| Position | 13C-NMR | 1H-NMR |
|---|---|---|
| 6-O-Glc | | |
| 1' | 104.08 | 4.91 (1H, d, J = 7.7 Hz, H-1') |
| 2' | 79.49 | 4.48 (1H, m, H-2') |
| 3' | 80.55 | 4.38 (1H, m, H-3') |
| 4' | 73.05 | 4.16 (1H, m, H-4') |
| 5' | 79.94 | 4.15 (1H, m, H-5') |
| 6' | 63.53 | 4.54 (1H, m, H-6'a), 4.32 (1H, m, H-6'b) |
| 2-O-Glc | | |
| 1'' | 104.32 | 6.02 (1H, d, J = 7.8 Hz, H-1'') |
| 2'' | 76.34 | 4.18 (1H, m, H-2'') |
| 3'' | 78.64 | 3.99 (1H, m, H-3'') |
| 4'' | 72.34 | 4.12 (1H, m, H-4'') |
| 5'' | 79.11 | 4.27 (1H, m, H-5'') |
| 6'' | 63.93 | 4.54 (1H, m, H-6''a), 4.32 (1H, m, H-6''b) |

[Test Example 1] Comparison of Activity of Estrogen Receptors

The following experiment was carried out to investigate whether the ginseng seed-derived ginsenoside GS #10 according to an exemplary embodiment of the present disclosure can regulate the activity of estrogen receptors.

After treating each of the novel ginsenoside GS #10 according to an exemplary embodiment of the present disclosure and other ginsenosides GS #01 to GS #06 isolated from the ginseng seed extract with a human ERα/β reporter assay panel (#IB00421-48P; Indigo Bioscience) at a concentration of 10 µg/mL for 24 hours, the increase of the activity of the estrogen receptors ERα and ERβ was analyzed. The #IB00421-48P kit comprises cells in which ERα and ERβ are overexpressed, respectively, and comprises the ERE-luc reporter gene. If the activity of the ER is increased by treating with the example or a comparative example, ERα and ERβ bind to ERE, thereby inducing the expression of luciferase. Therefore, the activity of ERα and ERβ can be measured by measuring the light intensity of the cells. As the comparative example, a methanol extract of ginseng seed (seeds of Panax ginseng) used for the isolation of the ginsenosides in Example 1 was used. It comprises the novel ginsenoside GS #10 at a small content of about 0.2% w/w.

Figure 11:
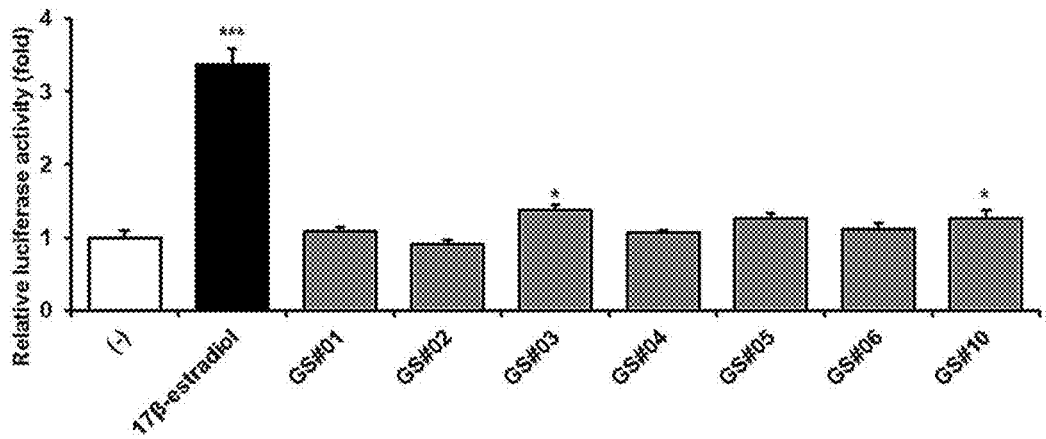
FIG. 11 compares the effect of regulating the activity of the estrogen receptor ERα of GS #10, which is a novel ginsenoside of the present disclosure isolated from a ginseng seed extract, with ginsenosides GS #01 to GS #06 as comparative examples (*$P<0.001$ vs. (−), $P<0.01$ vs. (−), *$P<0.05$ vs. (−)).
Figure 12:
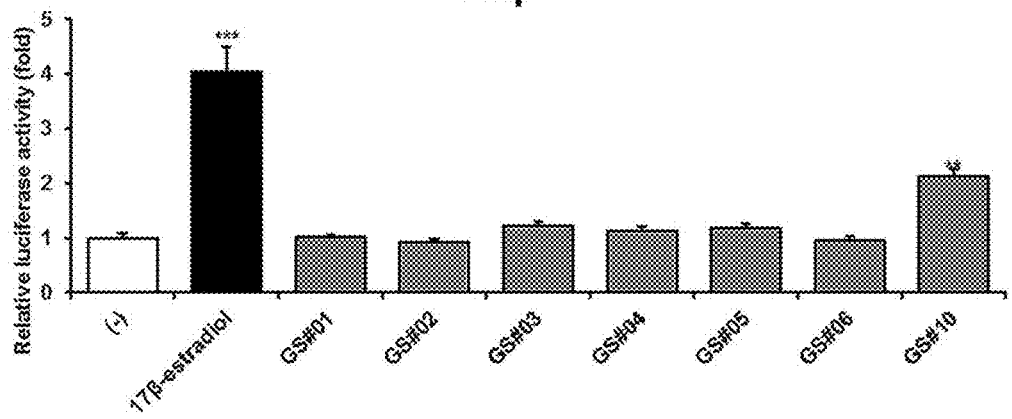
FIG. 12 compares the effect of regulating the activity of the estrogen receptor ERβ of GS #10, which is a novel ginsenoside of the present disclosure isolated from a ginseng seed extract, with ginsenosides GS #01 to GS #06 as comparative examples (*$P<0.001$ vs. (−), $P<0.01$ vs. (−), *$P<0.05$ vs. (−)).
Figure 13:
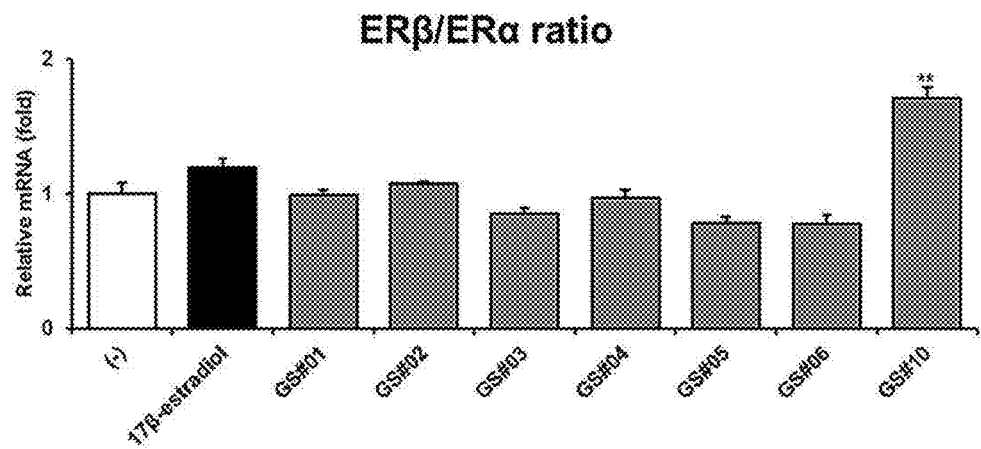
FIG. 13 compares the activity ratio of the estrogen receptors ERβ to ERα for GS #10, which is a novel ginsenoside of the present disclosure isolated from a ginseng seed extract, with ginsenosides GS #01 to GS #06 as comparative examples (**$P<0.01$ vs. (−)).

17β-Estradiol comprised in the #IB00421-48P kit was used as a positive control group. It is reported that, although the increased activity of the estrogen receptors ERα and ERβ can lead to alleviation of menopausal symptoms, ERs are overexpressed in more than 70% of breast cancer cells, mainly due to increased ERα (ESR1) (see Deroo B J et al., J Clin Invest 116:561 (2006)). As shown in FIG. 11, among the ginseng seed-derived ginsenosides, GS #03 (ginsenoside Re), GS #05 ginsenoside Rb1) and GS #10 slightly increased the activity of ERα. In contrast, as shown in FIG. 12, only GS #10 according to an exemplary embodiment of the present disclosure activated ERβ from among the ginseng seed-derived ginsenosides. FIG. 13 shows the activity ratio of ERβ to ERα based on the results of FIG. 11 and FIG. 12. Among the ginseng seed-derived ginsenosides, only the novel ginsenoside GS #10 according to an exemplary embodiment of the present disclosure increased the activity of both ERα and ERβ, and the activity ratio of ERβ to ERα was greater than 1 with about 1.7. This is a remarkably improved effect as compared to the positive control group.

Figure 14:
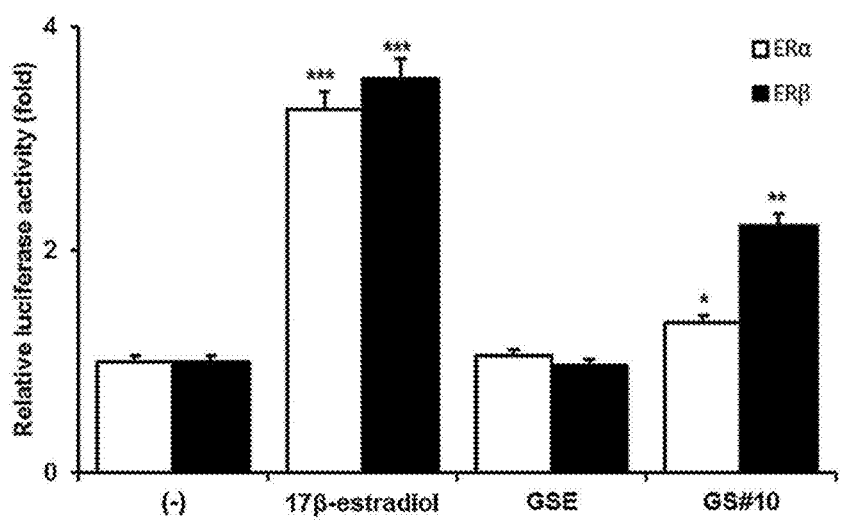
FIG. 14 compares the effect of regulating the activity of the estrogen receptors ERα and ERβ of GS #10, which is a novel ginsenoside of the present disclosure isolated from a ginseng seed extract, with a ginseng seed extract (GSE) as a comparative example (*$P<0.001$ vs. (−), $P<0.01$ vs. (−), *$P<0.05$ vs. (−)).

In addition, whereas the ginseng seed extract (GSE) itself showed no effect of increasing the activity of the estrogen receptors ERα and ERβ, the novel ginsenoside GS #10 according to an exemplary embodiment of the present disclosure, which is a fraction isolated and purified from the ginseng seed extract (GSE), had an effect of increasing the activity of the estrogen receptors ERα and ERβ, as shown in FIG. 14. This means that the effect of preventing or improving postmenstrual symptoms by increasing the activity of the estrogen receptors is intrinsic only to the novel ginsenoside GS #10 according to an exemplary embodiment of the present disclosure and is not found in the ginseng seed extract.

[Test Example 2] Comparison of Growth Activity of Breast Cancer Cells

It was found out in Test Example 1 that, whereas the positive control group 17β-estradiol increases the activity of both ERα and ERβ, the novel ginsenoside GS #10 according to an exemplary embodiment of the present disclosure increases the activity of ERβ more as compared to ERα (FIG. 13). The activation of ERα increases the risk of breast cancer because of increased growth and cell division of breast cancer cells, but ERβ suppresses the cancer cell growth by inhibiting the activity of ERα. Therefore, it is expected that the risk of breast cancer, which is known as the representative side effect of estrogen therapy, will be decreased significantly if the increase in the activity of ERβ is higher than ERα. Thus, it was investigated by growing MCF-7 breast cancer cells (ATCC) whether the novel ginsenoside GS #10 according to an exemplary embodiment of the present disclosure shows the side effect of promoting cancer cell growth. Specifically, MCF-7 breast cancer cells (ATCC) were treated with the novel ginsenoside GS #10 according to an exemplary embodiment of the present disclosure and the ginsenosides GS #01 to GS #06 isolated from the ginseng seed extract at a concentration of 10 µg/mL, respectively, for 48 hours and then the number of the cells was counted using a cell counting device (Countess, Thermo Fisher Scientific).

Figure 15:
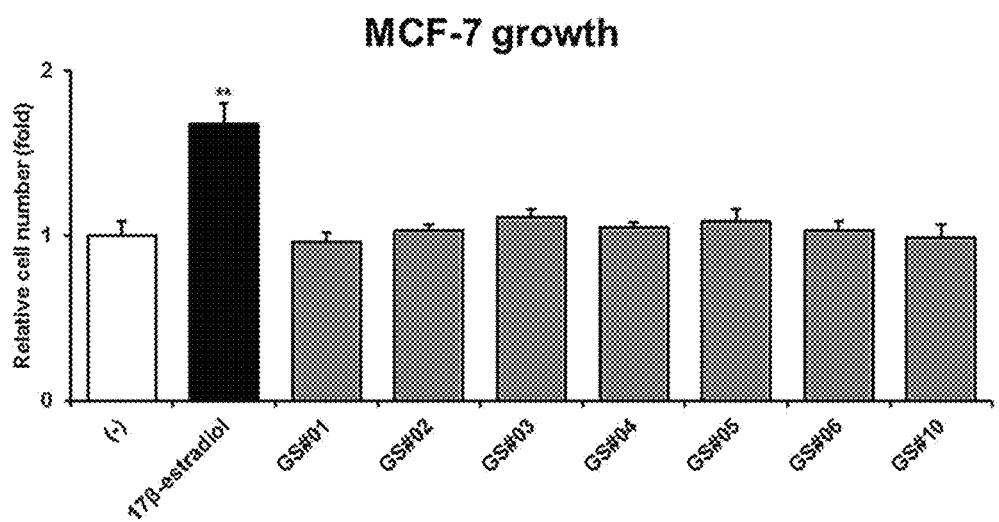
FIG. 15 shows a result of comparing the growth of MCF-7 breast cancer cells for GS #10, which is a novel ginsenoside of the present disclosure isolated from a ginseng seed extract, with ginsenosides GS #01 to GS #06 as comparative examples in order to investigate whether the incidence of breast cancer as a side effect is increased (**$P<0.01$ vs. (−)).

As shown in FIG. 15, despite the superior effect of activating ERβ, 17β-estradiol promoted the growth of the breast cancer cells because it also activated ERα. In contrast, the novel ginsenoside GS #10 according to an exemplary embodiment of the present disclosure did not show such a side effect. This means that the novel ginsenoside GS #10 according to an exemplary embodiment of the present disclosure has the effect of activating the estrogen receptors without the side effect of estrogen therapy.

[Test Example 3] Comparison of Activity of Estrogen Receptors

The effect of preventing or improving menopausal symptoms of the novel ginsenoside GS 410 according to an exemplary embodiment of the present disclosure was compared with that of ginsenosides Rg1, Rg3 and Rb1 (purchased from Sigma), which are red ginseng marker compounds, as comparative examples. Ginsenoside Rg3 has the following chemical structure. The experiment was performed in the same manner as in Test Example 1.

[Chemical Formula 2]

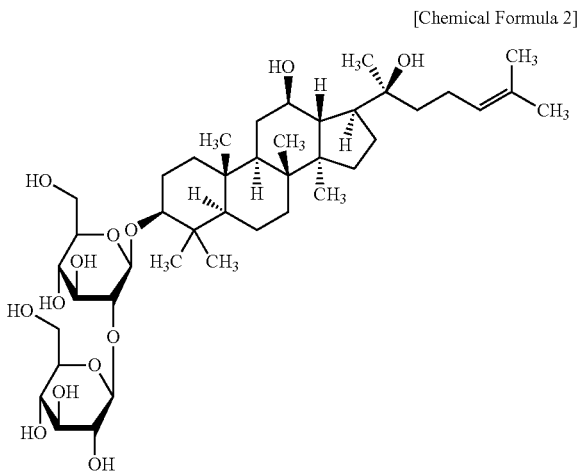

Figure 16:
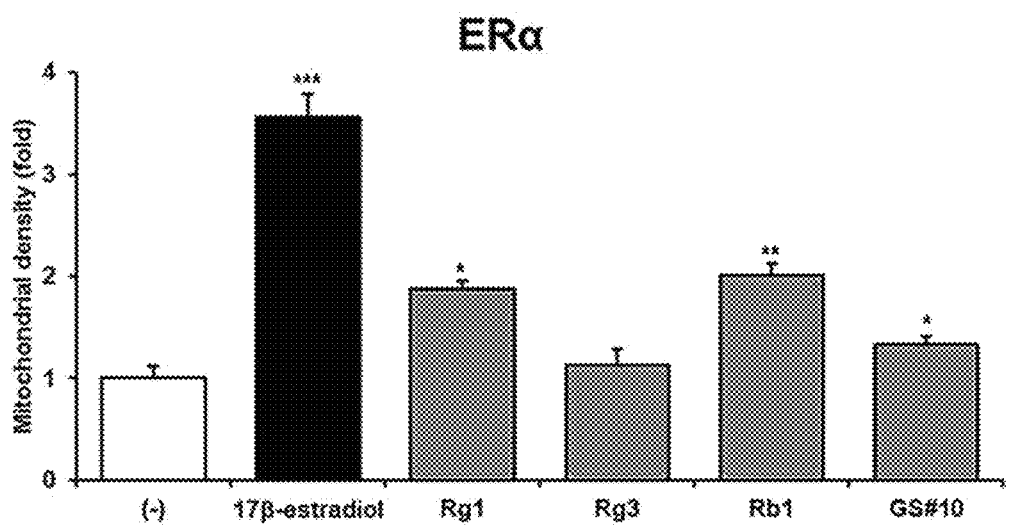
FIG. 16 compares the effect of regulating the activity of the estrogen receptor ERα for ginsenosides Rg1, Rg3 and Rb1, which are marker compounds of red ginseng, and GS #10, which is a novel ginsenoside of the present disclosure (*$P<0.001$ vs. (−), $P<0.01$ vs. (−), *$P<0.05$ vs. (−)).
Figure 17:
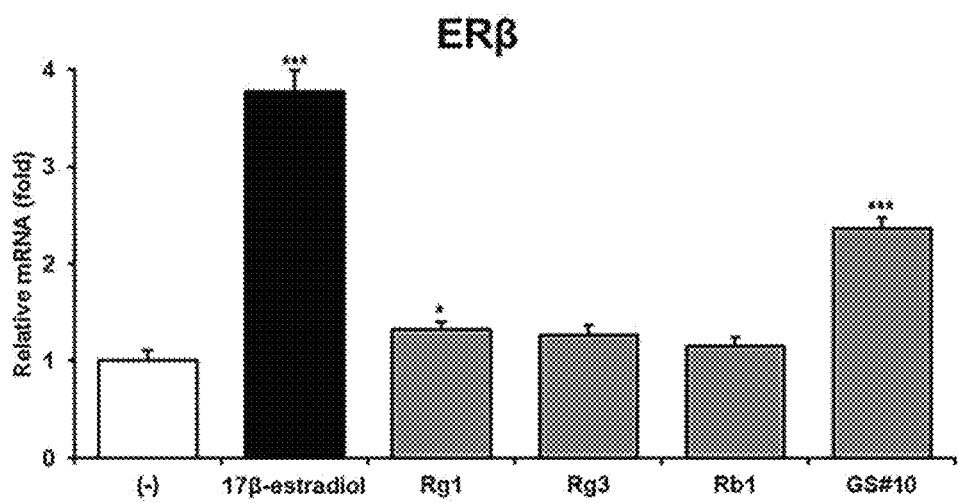
FIG. 17 compares the effect of regulating the activity of the estrogen receptor ERβ for ginsenosides Rg1, Rg3 and Rb1, which are marker compounds of red ginseng, and GS #10, which is a novel ginsenoside of the present disclosure (*$P<0.001$ vs. (−), $P<0.01$ vs. (−), *$P<0.05$ vs. (−)).

As shown in FIG. 16 and FIG. 17, all of the red ginseng marker compounds, the ginsenosides Rb1, Rg1 and Rg3, activated the estrogen receptors to some extent. But, peculiarly, the novel ginsenoside GS 410 according to an exemplary embodiment of the present disclosure showed at least 3 times higher activity of ERβ as compared to the ginsenosides Rg1 and Rb1 (Rg1 32%, Rb1 15%, GS #10 136%), whereas the increase in the activity of ERα was not higher than Rg1 and Rb1. This suggests that the novel ginsenoside GS #10 according to an exemplary embodiment of the present disclosure is pharmaceutically applicable for commercial use as an agent for preventing or improving menopausal symptoms since it exhibits superior effect of activating the estrogen receptors with low risk of breast cancer because the activity ratio of ERβ to ERα is higher than the ginsenosides Rb1, Rg1 and Rg3, which are red ginseng marker compounds.

[Test Example 4] Cytotoxicity

Cell growth in the presence of the novel ginsenoside GS #10 according to an exemplary embodiment of the present disclosure was evaluated using a cell counting kit (CCK-8) in order to exclude the possibility that the ginsenoside may affect the effect of preventing or improving menopausal symptoms through cytotoxic activity. The experimental method is as follows.

10 μL of a CCK-8 reagent was added to SH-SY5Y cells (Dojindo, Md., USA) in a 96-well plate and left at 37° C. for 2 hours. Then, absorbance was measured at 450 nm. Cell viability was represented as the percentage (%) of the absolute optical density of each sample relative to an untreated sample. The concentration of the novel ginsenoside GS #10 according to an exemplary embodiment of the present disclosure in the medium in which the cells were cultured was 0.1, 1, 5, 10, 20 and 50 μM, respectively.

Figure 18:
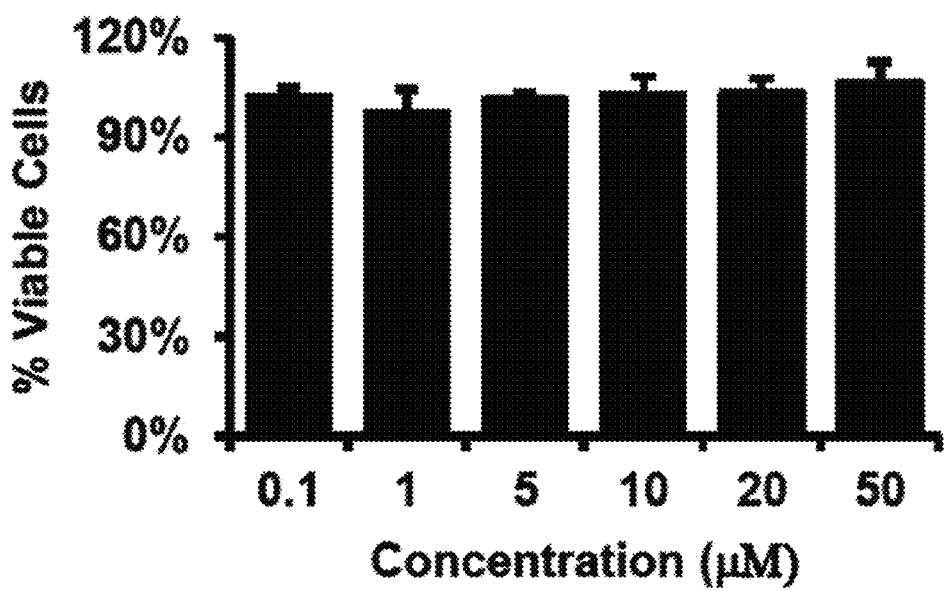
FIG. 18 shows a result of investigating the cell viability (%) for Compound 10 (GS #10), which is a novel ginsenoside of the present disclosure (*$P<0.001$ vs. (−), $P<0.01$ vs (−), *$P<0.05$ vs. (−)).

As shown in FIG. 18, the novel ginsenoside GS #10 according to an exemplary embodiment of the present disclosure did not exhibit cytotoxicity up to 50 μM. This result indicates that the novel ginsenoside according to an exemplary embodiment of the present disclosure can exhibit an effect of preventing or improving menopausal symptoms without adversely affecting cell viability.

Hereinafter, the present disclosure will be described in detail through formulation examples. However, various other formulations are also possible and the following formulation examples do not limit the scope of the present disclosure.

[Formulation Example 1] Tablet

After mixing 100 mg of ginsenoside PG-RT$_8$, 400 mg of lactose, 400 mg of corn starch and 2 mg of magnesium stearate, a tablet was prepared by tableting the mixture according to a common method.

[Formulation Example 2] Capsule

After mixing 100 mg of ginsenoside PG-RT$_8$, 400 mg of lactose, 400 mg of corn starch and 2 mg of magnesium stearate, a capsule was prepared by filling the mixture in a gelatin capsule according to a common method.

[Formulation Example 3] Granule

After mixing 50 mg of ginsenoside PG-RT$_8$, 250 mg of anhydrous crystalline glucose and 550 mg starch, the mixture was formed into a granule using a fluidized-bed granule and then filled in a pouch.

[Formulation Example 4] Drink

After mixing 50 mg of ginsenoside PG-RT$_8$, 10 g of glucose, 0.6 g of citric acid and 25 g of oligosaccharide syrup and adding 300 mL of purified water, 200 mL of the mixture was filled in a bottle. After the bottle was filled, a drink was prepared by sterilizing the content at 130° C. for 4-5 seconds.

[Formulation Example 5] Caramel Formulation

A caramel was prepared by mixing 50 mg of ginsenoside PG-RT$_8$, 1.8 g of corn syrup, 0.5 g of skim milk, 0.5 g of soy lecithin, 0.6 g of butter, 0.4 g of hydrogenated vegetable oil, 1.4 g of sugar, 0.58 g of margarine and 20 mg of table salt.

[Formulation Example 6] Health Food

TABLE 3

| Ingredients | Contents |
| --- | --- |
| PG-RT$_8$ | 100 mg |
| Vitamin mixture | |
| Vitamin A acetate | 70 μg |
| Vitamin E | 1.0 mg |
| Vitamin B$_1$ | 0.13 mg |
| Vitamin B$_2$ | 0.15 mg |
| Vitamin B$_6$ | 0.5 mg |
| Vitamin B$_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Mineral mixture | |
| Ferrous sulfate | 1.75 mg |
| Zinc oxide | 0.82 mg |
| Magnesium carbonate | 25.3 mg |
| Potassium phosphate monobasic | 15 mg |
| Calcium phosphate dibasic | 55 mg |
| Potassium citrate | 90 mg |
| Calcium carbonate | 100 mg |
| Magnesium chloride | 24.8 mg |

Although the above composition of the vitamin and mineral mixtures was presented as an example relatively suitable for health foods, the composition may be varied as desired. According to a common health food preparation method, the above ingredients may be mixed and then prepared into a granule, which may be used to prepare a health food composition according to a common method.

[Formulation Example 7] Health Drink

TABLE 4

| Ingredients | Contents |
| --- | --- |
| PG-RT$_8$ | 10 mg |
| Citric acid | 1000 mg |
| Oligosaccharide | 100 g |
| Plum concentrate | 2 g |
| Taurine | 1 g |
| Purified water | Balance |
| Total volume | 900 mL |

As shown in the above table, a balance of purified water was added to make a total volume of 900 mL, and the above ingredients were mixed according to a common method for preparing a healthy drink, and heated at 85° C. under stirring for about 1 hour. Then, the resulting solution was filtered and collected in a sterilized 2-L container, sterilized, sealed, and then stored in a refrigerator for use in preparation of a healthy drink composition.

[Formulation Example 8] Injection

An injection was prepared according to a common method with the composition described in the following table.

TABLE 5

| Ingredients | Contents |
| --- | --- |
| PG-RT$_8$ | 10-50 mg |
| Sterile distilled water for injection | Proper amount |
| pH control agent | Proper amount |

The present disclosure may provide the following exemplary embodiments.

As a first exemplary embodiment, there may be provided a method for preventing or improving menopausal symptoms, which comprises administering an effective amount of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof to a subject in need thereof.

As a second exemplary embodiment, there may be provided the method according to the first exemplary embodiment, wherein the (20S,24R)-6-O-β-D-glucopyranosyl(1→2)-β-D-glucopyranoside-dammar-3-one-20,24-epoxy-6a,12b,25-triol has a structure of Chemical Formula 1.

[Chemical Formula 1]

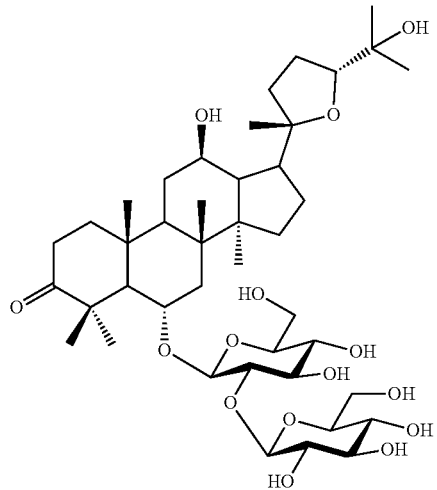

As a third exemplary embodiment, there may be provided the method according to the first exemplary embodiment or the second exemplary embodiment, wherein the (20S,24R)-6-O-β-D-glucopyranosyl(1→2)-β-D-glucopyranoside-dammar-3-one-20,24-epoxy-6a,12b,25-triol is extracted from ginseng seed.

As a fourth exemplary embodiment, there may be provided the method according to any of the first to third exemplary embodiments, wherein the menopausal symptoms comprise one or more of dizziness, sleep disorder, hot flashes, osteoporosis, night sweats, depression, headache and fatigue.

As a fifth exemplary embodiment, there may be provided the method according to the first to fourth exemplary embodiments, wherein, when the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof is administered to the subject, the ratio of the activity of the estrogen receptors ERβ (estrogen receptor β) to ERα (estrogen receptor α) is 1.1 times or greater.

As a sixth exemplary embodiment, there may be provided the method according to any of the first to fifth exemplary embodiments, wherein the administration amount of the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof is from 0.05 mg/kg/day to 10 g/kg/day.

As a seventh exemplary embodiment, there may be provided the method according to any of the first to sixth exemplary embodiments, wherein the subject is a subject in which the activity of estrogen receptors is decreased.

As an eighth exemplary embodiment, there may be provided the method according to any of the first to seventh exemplary embodiments, wherein the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof is administered transdermally.

As a ninth exemplary embodiment, there may be provided the method according to any of the first to eighth exemplary embodiments, wherein the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof is administered orally or parenterally.

The above exemplary embodiments have been disclosed for the purpose of illustration, and the foregoing description is not intended to limit the scope of the present disclosure. Accordingly, various modifications, variations and substitutions may occur to those of ordinary skill in the art without departing from the meaning and scope of the present disclosure.

What is claimed is:

1. A method for inhibiting, delaying or improving menopausal symptoms, comprising administering an effective amount of (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof to a subject in need thereof,
   wherein the menopausal symptoms are one or more of dizziness, hot flashes, osteoporosis, night sweats and headache.

2. The method according to claim 1, wherein the (20S,24R)-6-O-β-D-glucopyranosyl(1→2)-β-D-glucopyranoside-dammar-3-one-20,24-epoxy-6a,12b,25-triol is extracted from ginseng seed.

3. The method according to claim 1, wherein, when the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof is administered to the subject, the ratio of the activity of the estrogen receptors ERβ (estrogen receptor β) to ERα (estrogen receptor α) is 1.1 times or greater.

4. The method according to claim 1, wherein the administration amount of the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof is from 0.05 mg/kg/day to 10 g/kg/day.

5. The method according to claim 1, wherein the subject is a subject in which the activity of estrogen receptors is decreased.

6. The method according to claim 1, wherein the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof is administered transdermally.

7. The method according to claim 1, wherein the (20S,24R)-6-O-β-D-glucopyranosyl(1→2)-β-D-glucopyranoside-dammar-3-one-20,24-epoxy-6a,12b,25-triol, a pharmaceutically acceptable salt thereof, a hydrate thereof or a solvate thereof is administered orally or parenterally.

* * * * *